United States Patent
Lifshotz et al.

(10) Patent No.: US 12,288,624 B2
(45) Date of Patent: Apr. 29, 2025

(54) COMPLIANCE DATAFLOW MANAGEMENT

(71) Applicant: Hatch Compliance Inc., Charlotte, NC (US)

(72) Inventors: Michael Lifshotz, Charlotte, NC (US); Renee Douthat, Charlotte, NC (US); Christopher Rivera, Charlotte, NC (US)

(73) Assignee: Hatch Compliance Inc., Charlotte, NC (US)

( * ) Notice: Subject to any disclaimer, the term of this patent is extended or adjusted under 35 U.S.C. 154(b) by 246 days.

(21) Appl. No.: 17/811,529

(22) Filed: Jul. 8, 2022

(65) Prior Publication Data

US 2024/0013927 A1    Jan. 11, 2024

(51) Int. Cl.
*G16H 50/70*   (2018.01)
*G06Q 50/26*   (2012.01)

(52) U.S. Cl.
CPC .......... *G16H 50/70* (2018.01); *G06Q 50/265* (2013.01)

(58) Field of Classification Search
None
See application file for complete search history.

(56) References Cited

U.S. PATENT DOCUMENTS

| | | | |
|---|---|---|---|
| 8,682,697 B1* | 3/2014 | Harris, Sr. | ............. G06Q 10/10 705/4 |
| 9,049,314 B2 | 6/2015 | Pugh et al. | |
| 10,929,983 B2 | 2/2021 | Hanina et al. | |
| 11,741,409 B1* | 8/2023 | Scotney | ......... G06Q 10/063114 705/317 |
| 2010/0305977 A1* | 12/2010 | Hogan | ................... G06Q 40/08 706/47 |
| 2013/0263206 A1* | 10/2013 | Nefedov | ............... G06F 21/604 726/1 |
| 2018/0032855 A1* | 2/2018 | Wang | ..................... G06Q 30/04 |
| 2018/0285887 A1* | 10/2018 | Maung | ................. G06Q 30/018 |
| 2020/0058381 A1* | 2/2020 | Patel | ...................... G16H 10/60 |
| 2020/0234816 A1* | 7/2020 | De Armas | ............. G16H 70/20 |

(Continued)

FOREIGN PATENT DOCUMENTS

WO    WO 2022/167241 A1 *   8/2022   ............. G06Q 10/06

OTHER PUBLICATIONS

Casati et al., Compliance Aware Cross-Organization Medical Record Sharing, 2013 IFIP/IEEE International Symposium on Integrated Network Management (IM 2013).*

(Continued)

*Primary Examiner* — David J Stoltenberg
(74) *Attorney, Agent, or Firm* — Polygon IP, LLP

(57) ABSTRACT

Described herein is a compliance dataflow management system. The system may include a plurality of different databases. The system may be configured to provide for workflow that are in conformance of regulations and/or requirements for specific jurisdictions. Furthermore, aspects of the system may allow for automatic updating of compliance systems in a manner that allows for resource savings for automated compliance software. Additionally, the system may include automated auditing systems, allowing for compliance to be determined in a quick and resource efficient manner while allowing for privacy and security to be maintained.

20 Claims, 12 Drawing Sheets

(56) References Cited

U.S. PATENT DOCUMENTS

2022/0198053 A1* 6/2022 Madhavan .............. G06F 21/31
2023/0368214 A1* 11/2023 Suryanarayana ...... G06Q 50/18

OTHER PUBLICATIONS

Tresp et al. Going Digital: A Survey on Digitalization and Large-Scale Data Analytics in Healthcare, Proceedings of the IEEE | vol. 104, No. 11, Nov. 2016.*
Gutiérrez et al., HealthyBlock: Blockchain-Based IT Architecture for Electronic Medical Records Resilient to Connectivity Failures, Int. J. Environ. Res. Public Health 2020, 17, 7132; doi: 10.3390/ijerph17197132.*

* cited by examiner

COMPLIANCE DATAFLOW MANAGEMENT

BACKGROUND

Regulatory compliance is critical for organizations that are operating within the healthcare space, as well as in other fields. Typically, regulatory compliance is manually performed, with a compliance officer of an organization manually determining the forms and information that are needed to be compliant for any single matter of an organization. Such a technique requires a large amount of manpower and is also susceptible to human error, as regulations may regularly change. In certain situations, the compliance officer may forget about changes or even be unaware of such changes, leading to error and non-compliance.

SUMMARY

Described are methods and systems for compliance dataflow management. In a certain embodiment, a system may be described. The system may include a jurisdiction database, a returns database, a communication module, and an automated auditor, communicatively coupled to the jurisdiction database, the returns database, and the communication module, the automated auditor configured to perform operations including: determining that an audit condition associated with a first entity has been met, determining, from the first returns data from the returns database, a first jurisdiction associated with the first entity, obtaining jurisdiction requirement data associated with the first jurisdiction from the jurisdiction database, analyzing the jurisdiction requirement data to determine compliance requirements for the first jurisdiction, determining, based on the first returns data and the compliance requirements, a compliance status for the first entity, and providing, with the communication module, the compliance status to a user device associated with the first entity.

In a further embodiment, another system may be described. The system may include an Application Programming Interface (API) gateway and a compliance platform. The API gateway may be configured to perform first operations including: receiving a first API request from a user device, where the first API request includes authentication data, determining validity of the authentication data, and providing, based on determining the validity of the authentication data, the first API request to a compliance platform. The compliance platform may include one or more API modules, including at least a workflow API module, a memory, and a processor, configured to receive instructions from the memory to perform second operations including: receiving the first API request from the API gateway; determining that the first API request includes a request to access the workflow API module; and providing the user device with access to the workflow API module. The workflow API module may be configured to: receive a first compliance request including jurisdiction data identifying a first jurisdiction for compliance, analyze the jurisdiction data to determine the first jurisdiction for compliance, obtain, based on the first jurisdiction for compliance, jurisdiction requirement data associated with the first jurisdiction, analyze the jurisdiction requirement data to determine form requirements for compliance, and create a first jurisdiction workflow based on the form requirements for compliance.

In another embodiment, a method may be described. The method may include receiving a set of first data configured for training a dataflow compliance machine learning module, where the first data includes a plurality of datapoints, each datapoint including at least a jurisdiction element and a subject matter element, preparing training data, where the preparing the training data includes: creating a plurality of sets of the first data, preparing, based on the jurisdiction element, a first set of the plurality of sets of the first data, and preparing, based on the subject matter element, a second set of the plurality of sets of the first data, and training the machine learning module with the first set and the second set.

Illustrative, non-exclusive examples of inventive features according to the present disclosure are described herein. These and other examples are described further below with reference to figures.

BRIEF DESCRIPTION OF THE DRAWINGS

The disclosure may best be understood by reference to the following description taken in conjunction with the accompanying drawings, which illustrate various embodiments.

DETAILED DESCRIPTION

In the following description, specific details are set forth to provide illustrative examples of the systems and techniques described herein. The presented concepts may be practiced without some, or all, of these specific details. In other instances, well known process operations have not been described in detail to avoid unnecessarily obscuring the described concepts. While some concepts will be described with the specific examples, it will be understood that these examples are not intended to be limiting.

Some implementations of the disclosed systems, apparatus, methods and computer program products are configured for implementing a compliance dataflow management system (e.g., for compliance with healthcare regulations and/or procedures, such as for compliance with healthcare laws, for compliance with human resources procedures, such as laws related to human resources and/or for internal human resources procedures, and/or for compliance with requirements of industry standards, accrediting agencies, or with insurance regulations). Various aspects of the system may be configured to manage data in an environment where privacy and security are paramount. Furthermore, aspects of the system may allow for automatic updating of compliance systems in a manner that allows for resource savings for automated compliance software. Such automatic updating may include updating systems so that subsequent data (e.g., forms) provided by the system are fully up to date and, thus, do not require the correction of incorrect forms. Correction of incorrect forms stored on servers require significant network and memory resources; automatic updating may allow for conservation of such resources. Additionally, aspects of the system may further include automated auditing systems, allowing for compliance to be determined in a quick and resource efficient manner while allowing for privacy and security to be maintained. Furthermore, the system may include various Application Programming Interfaces (APIs), and aspects of the system may be utilized through the various APIs.

In various embodiments, the disclosed systems and techniques may be used for compliance with various industry and/or private party regulations and/or requirements. Though reference may be made to compliance with certain industries (e.g., the healthcare industry, such as the behavioral healthcare industry), it is appreciated that the system and techniques described herein may be applicable to any industry and/or application where compliance with certain requirements is needed.

Figure 1:
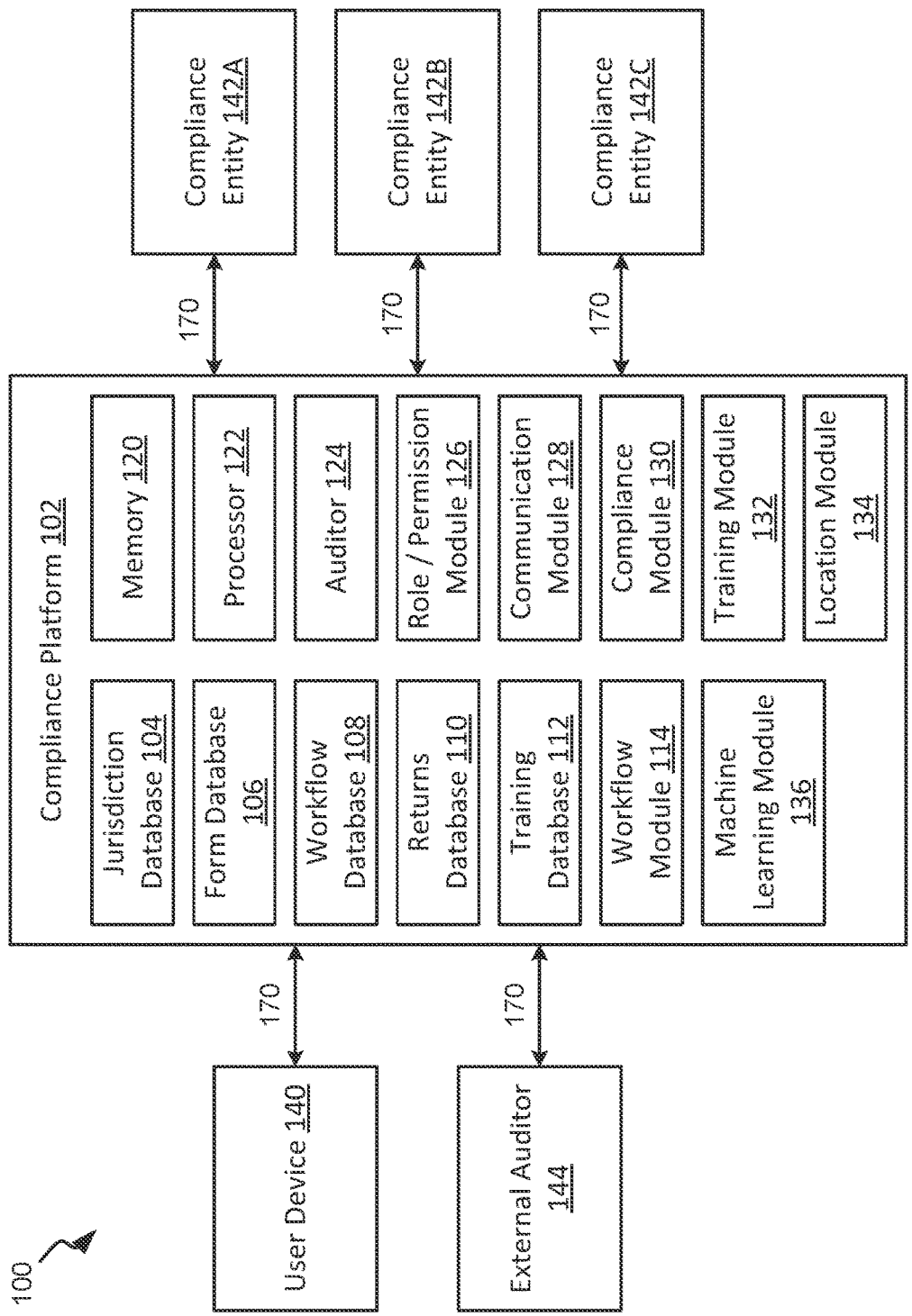
FIG. 1 illustrates a block diagram of an example system for compliance dataflow management, in accordance with some embodiments.

FIG. 1 illustrates a block diagram of an example system for compliance dataflow management, in accordance with some embodiments. FIG. 1 illustrates system 100 that includes compliance platform 102, user device 140, external auditor 144, and a plurality of compliance entities 142. It is appreciated that, for the purposes of this disclosure, when an element includes a plurality of similar elements distinguished by a letter following the ordinal indicator (e.g., compliance entities "142A," "142B," and "142C") and reference is made to only the ordinal indicator itself (e.g., "142"), such a reference is applicable to all the similar elements.

Within system 100, the various portions are communicatively coupled via communications network 170. Communications network 170 may be any wired or wireless communications connection that allows for data to be sent. Network 170 may be, for example, a wired Ethernet connection or a wireless connection such as WiFi, 3G, 4G, 5G, or another such connection that allows for data to be transmitted. In various embodiments, the various components of the systems described herein may utilize one, some, or all of such data connections to communicate and/or receive data.

Compliance platform 102 may include jurisdiction database 104, form database 106, workflow database 108, returns database 110, training database 112, workflow module 114, memory 120, processor 122, auditor 124, role-permission module 126, communication module 128, compliance module 130, training module 132, location module 134, and machine learning module 136. The various elements of compliance platform 102 may be electromagnetically (e.g., communicatively) coupled with each other. Such coupling may allow for various elements of compliance platform 102 to send and receive data from other elements. In various embodiments, the databases and modules of compliance platform 102 may, in certain embodiments, be physically separate from each other (e.g., may be separate components and/or physical databases) to provide for increased privacy and data security. Furthermore, the database and/or modules may be configured to perform separate portions of compliance and/or store data of separate formats (e.g., data that includes different types of information or sensitive information). Thus, separation of the databases and modules allows for the techniques to be performed and data to be accessed in a resource efficient manner and for data privacy to be maintained, as described herein.

Memory 120 may be any type of memory device configured to store data and/or instructions. Memory 120 may be, for example, a harddrive, a solid state device, and/or random access memory (RAM) and may include transitory or non-transitory computer-readable media. Memory 120 may be configured to store instructions for performing the techniques described herein. Such instructions may be communicated to various elements of compliance platform 102, such as processor 122.

Processor 122 may be a single or multi-core processor. As described herein, processor 122 may be configured to perform operations of compliance platform 102, as described herein. Processor 122 may be any type of single or multi-core processor that allows for electronic data processing.

Jurisdiction database 104, form database 106, workflow database 108, returns database 110, and training database 112 may be databases that include, for example, harddrives, solid state devices, cloud storage, random access memory (RAM), and/or other such storage devices. The various databases may be separate from each other and may, thus, each be configured to store data of a specific type to maintain privacy and data security for compliance platform 102.

Thus, for example, jurisdiction database 104 may be configured to store data related to various specific jurisdictions. For example, jurisdiction database 104 may be configured to store data related to the compliance requirements of a plurality of different jurisdictions associated with users of jurisdiction database 104 (e.g., the users may be operating or doing business within such jurisdictions). Thus, for example, jurisdiction database 104 may be configured to store data indicating the requirements that are needed to comply with the requirements of the various jurisdictions (e.g., the types of data that are required to be provided to be in compliance for the jurisdiction). In various embodiments, reference to a "jurisdiction" may include locations that are traditionally associated with jurisdictions, but may also include other entities that require compliance, such as insurance entities, human resource entities, and/or other such entities. Thus, it is appreciated that, for the purposes of this disclosure, "jurisdiction" may refer to traditional geographical or legal entities, but may also refer to other entities for which compliance with certain regulations or requirements are needed.

In various embodiments, data required by the various jurisdiction for compliance may include, for example, name, date of birth, procedure performed, pricing, healthcare provider comments, prescription, and/or other such data. Jurisdiction database 104 may, thus, be compartmentalized into various different jurisdictions. The data required by each jurisdiction for a submission to be in compliance (e.g., via a form) may include one or more of such types of data. In various embodiments, jurisdiction database 104 may indicate the data required by each jurisdiction. In certain embodiments, jurisdiction database 104 may include data linking to the original source of the regulations and/or requirements and/or may include copies of the original documents themselves (e.g., compliance platform 102 may download the original documents for storage within jurisdiction database 104). In certain such embodiments, workflows that are provided to a user may include the links and/or copies of the original document, to allow for the user access to the original documents, for reference. Forms for completion and workflows to fill out the forms and comply with the requirements of the jurisdiction may be stored within form database 106 and workflow database 108, respectively. Returns database 110 may be configured to stored completed forms and/or returned data from workflows communicated to users, as such completed forms may include sensitive information that needs to comply with certain privacy requirements. Though reference may be made herein to workflows as forms, other embodiments may include workflows in the form of charts, graphs, and/or other such workflows. For the purposes of this disclosure, it is appreciated that "workflow" may refer to any instrument for compliance, such as instruments where users and/or other parties are required to provide data (e.g., answers or feedback).

Form database 106 may be configured to store form data. Such form data may include, for example, forms used for compliance for healthcare providers, professionals, patients, and/or other parties. In various embodiments, the forms stored within form database 106 may be blank forms without any sensitive information. In certain embodiments, the forms may be forms that are configured to be shared by a plurality of different jurisdictions and may include one or more categories (e.g., questions and/or entries for data) that are only needed for one or some of the plurality of jurisdictions. In certain embodiments, form database 106 may be configured to store and provide forms associated with specific subject matters. Thus, for example, the forms within form database 106 may be stored according to subject matter (e.g., different categories of compliance). Form database 106 may store a number of forms for each certain subject matter that is less than the total number of jurisdictions (e.g., within jurisdiction database 104).

Workflow database 108 may accordingly provide data so that the form is configured for the appropriate jurisdiction, allowing for one or more forms to be shared for a plurality of jurisdictions while being appropriate for use in each of the plurality of jurisdictions. Additionally or alternatively, workflow database 108 may receive form data and create an appropriate workflow for the user. Such a workflow may not be the form itself but may, instead, be various requests for data (e.g., questionnaires) provided to the user. Compliance platform 102 may then receive reply data from the user, in response to the requests for data and fill out the appropriate forms or provide or store the data as needed in order to meet compliance requirements (e.g., while certain compliance actions may require the submission of certain filled out forms, other compliances actions may only require that the entity obtain and store such data). Reply data may be stored within returns database 110 as returns data.

Workflow database 108 may be configured to store workflows associated with the forms. Workflow database 108 may, thus, store workflows that are required to complete forms provided by form database 106, according to the jurisdiction associated with the form (e.g., the jurisdiction for compliance). Thus, in various embodiments, form database 106 may be accessed to obtain the appropriate form and jurisdiction data may be accessed (e.g., from jurisdiction database 104) to determine the jurisdiction associated with the compliance. Based on the form used and the jurisdiction for compliance (e.g., the physical area, such as state, municipality, country, country, and/or other such, the healthcare provider, the insurance provider, and/or other such jurisdiction), data from workflow database 108 may be accessed to determine the portions of the form that is required to be completed for compliance within the jurisdiction.

Typically, for a form of a given subject matter (e.g., a form provided to indicate after patient care), each separate jurisdiction may include separate information requirements. Accordingly, each jurisdiction may include a form that is unique to the jurisdiction and the subject matter. Thus, if there is six different subject matters and 8 different jurisdictions, 48 different forms are required to be stored. Significant memory resources are required for storage and, furthermore, significant processing resources are required to select the appropriate form.

The configuration of compliance platform 102 allows for a single form to be shared between a plurality of jurisdictions that include different requirements, conserving memory and processing resources required to select the appropriate form. A single form may, additionally or alternatively, be shared between a plurality of subject matters, further conserving memory and processing resources. Furthermore, as regulations and requirements are constantly changing, especially when there is a large number of jurisdictions that may each include separate requirements, workflow database 108 may allow for simplified updating based on such changes, without the need to update the underlying form, further conserving changes and system resources. For example, in certain such situations, only the workflow may need to be updated as the underlying form may include sections that already conform with the updated requirements, but were not yet part of the workflow or included within the workflow as a non-conforming portion. Updating only the workflow may result in significant resource savings when conforming to updated regulations.

Returns database 110 may be configured to store data associated with one or more users and/or entities. Such data may, for example, be data that includes sensitive patient or employee information (e.g., name, date of birth, place of residence, family members, identification number, credit card number, and/or other such information). Returns database 110 may, thus, be separate from other databases to protect sensitive patient information. Returns database 110 may be configured to store forms that have been created and/or filled out for specific patients. Additionally or alternatively, returns database 110 may be configured to allow for limited access to data stored within returns database 110, as needed, according to the techniques described herein.

In certain embodiments, returns database 110 may be configured to include separate storage for each compliance entity (e.g., entity such as healthcare provider, healthcare group, and/or other such groups). The storage may be separate portions of a database and/or may be physically separate databases. Separating storage of different entities within returns database 110 may provide for increased data security.

Workflow module 114 may be configured to determine workflows according to the techniques described herein. Workflow module 114 may, in certain embodiments, be accessible or callable as an API, according to the techniques described herein. Thus, workflow module 114 may receive a request or call from a user device requesting a workflow for compliance and accordingly, determine the workflow. The workflow may be determined from data within the databases of compliance platform 102. It is appreciated that, for the purposes of this disclosure, the modules described herein may include or be implemented as APIs to allow for users to call upon the functions of the modules independently.

In various embodiments, such APIs may allow for third party users providing services to other parties to integrate the techniques within their systems, allowing for such third party users to provide services for the techniques described herein. For example, an insurance company may utilize the APIs described herein to provide for compliance services to their member doctors. In such embodiments, the third party users may utilize some or all of the services of compliance platform 102. Thus, for example, a third party user utilizing workflow module 114 as an API may also utilize and store data within the databases of compliance platform 102, or utilize data stored elsewhere. In other embodiments, such APIs may allow for an entity to access certain compliance techniques and utilize compliance platform 102 as their version of a virtual compliance officer, without requiring an actual in-organization compliance officer. Additionally or alternatively, the APIs may allow for members of the entity to provide data related to compliance, in order to meet the compliance requirements of the entity.

Training database 112 may be a database configured to provide data for training of machine learning module 136. Training database 112 may include data specifically curated to provide machine learning training. Data within training database 112 may be actual data that has been previously provided and/or may be data specifically configured for training of machine learning module 136. Such data may provide for training of machine learning module 136 to, for example, determine updates to requirements (e.g., of one or more jurisdictions and/or for one or more subject matters) and the changes required to various forms to be in compliance with the updated requirements.

Machine learning module 136 may be configured to perform machine learning of various techniques described herein. For example, machine learning module 136 may be a neural network and/or another module configured to receive data and provide outputs. Thus, for example, machine learning module 136 may be configured to receive data indicating regulatory updates within a jurisdiction (e.g., updated language) and determine the scope of the updates (e.g., the updates within a specific legal language) and/or be configured to determine situations where a user may be incorrectly provided responses to requested data.

In various jurisdictions, diction utilized to describe legal concepts and/or requirements may vary. For example, a first jurisdiction may utilize a first format (e.g., bullet points) and first diction (e.g., lots of traditional Latin phrases) while a second jurisdiction may utilize a second format (e.g., paragraphs) and second diction (e.g., plain language). Machine learning module 136 may be configured to receive data utilizing any such format, diction, and/or other aspects that are different and determine the regulatory requirements in a standardized format, based on training.

Based on the determined regulation changes, machine learning module 136 may be configured to determine any changes to the forms and/or to the workflow that is necessary to be in compliance with the updated regulations. Machine learning module 136 may then access the corresponding form and/or workflow and update accordingly. The updated form and/or workflow may be associated with the appropriate jurisdiction. Machine learning module 136 may then provide the updated form and/or workflow to form database 106 and/or workflow database 108 for storage and use. In other embodiments, machine learning module 136 may be configured to determine the requirements of new regulations and/or requirements and create new forms and/or workflows accordingly.

Auditor 124 may be configured to perform automated audits of portions of compliance database 102. Thus, for example, auditor 124 may be configured to audit the data of jurisdiction database 104, form database 106, workflow database 108, and/or completed responses within returns database 110 to determine if such data are still in compliance within their respective jurisdictions (e.g., the regulations and/or requirements of jurisdictions such as location, entity, subject matter, and/or other such jurisdictions). Auditor 124 may be configured to perform audits within regular timeframes (e.g., every hours) and may be configured to audit a certain portion of data (e.g., a set portion or a random portion of data) or all data. In various embodiments, auditor 124 may be granted certain permissions. The permissions may allow for auditor 124 to audit only certain portions of data or all data within compliance platform 102. Thus, the permissions may determine the level of audit performed by auditor 124.

Role/permission module 126 may be configured to determine the permission of auditor 124 as well as various users and allow such parties the appropriate access to the rest of compliance platform 102. Thus, for example, users within an organization may be authorized to access different levels of sensitive data (e.g., patient data). Based on the level of access, such users may be permitted to access various forms, workflows, and/or patient data from the respective databases. Role/permission module 126 may store data related to such permission levels, associated with various users, roles, and/or modules. Thus, role/permission module 126 may also determine appropriate permission levels for various modules of compliance platform 102 (e.g., for auditor 124).

Communication module 128 may be configured to communicate with various external devices, via communications network 170. Thus, for example, communication module 128 may be configured to communicate with user device 140, external auditor 144, and compliance entities 142 (e.g., receive and/or provide data to such elements). Such data may be utilized to perform the techniques described herein.

Compliance module 130 may be configured to determine compliance of workflows, according to various jurisdictions. Compliance module 130 may determine compliance within the regulations and/or requirements of various jurisdiction. In certain embodiments, compliance module 130 may be configured to determine compliance of workflows that are currently processing and/or created/stored on compliance platform 102, according to the techniques described herein, as opposed to auditor 124, which may be configured to determine compliance of data within databases (e.g., user stored data that have been provided by users) and, thus, determine compliance of an entity.

In certain embodiments, compliance module 130 and/or returns database 110 may be configured to receive grievance claims from various users. Such grievances may be provided by, for example, patients and/or employees of entities associated with compliance platform 102. Grievance data may be received and accordingly stored within returns database 110. Grievance data may be provided to, for example, auditor 124 and/or external auditor 144 to determine compliance of the entity identified associated with the grievance data with the regulations and/or requirements of various jurisdictions. In certain embodiments, grievance data may affect the compliance status of the entity.

Determination of conformance/compliance of workflows to regulations and auditing data is more efficiently performed separately, as workflows are determined in the moment, while auditing may possibly involve auditing based on updates to regulations or requirements. The configuration of compliance platform 102 allows for compliance module 130 to be more efficiently configured to determine compliance of workflows in progress while auditor 124 may be configured to determine data to be audited and audit such data.

Training module 132 may be configured to provide for training of various users according to the regulations. Thus, training module 132 may receive data directed to jurisdictions, forms, workflows and/or other data and provide training regimes to users for utilization of workflows provided herein. In various embodiments, a user may request compliance with a jurisdiction and a workflow may be provided in response. Training module 132 may provide training instructions for completing the workflow. In other embodiments, training module 132 may provide general instructions completing workflows, not associated with specific workflows.

In further embodiments, training module 132 may be configured to provide training to members of an entity so that the entity may be in compliance with rules, regulations, and/or requirements of a jurisdiction. Accordingly, for example, jurisdiction database 104 may further include data on techniques for training members of an entity so that the entity is in compliance. In another embodiment, machine learning module 136 may, based on the jurisdiction data and, possibly, training data that includes existing training techniques, determine training programs to be provided to users/entities in order to bring the entity within compliance.

Location module 134 may be configured to receive location data from user device 140 and/or another electronic device. Location module 134 may, thus, receive location data associated with compliance from an electronic device. Such location data may include, for example, GPS or other location data from a user device (e.g., a user device of a healthcare requester or account holder) and/or from a provider (e.g., a healthcare provider requiring compliance services).

User device 140 may be a user device of a user of compliance platform 102. Such a user may be, for example, a user associated with an entity that needs to be in compliance (e.g., a healthcare provider), a patient, and/or another such user. User device 140 may be, for example, desktop computing devices, portable computing devices (e.g., laptops, tablets, smartphones, and/or other electronic devices), wearable devices, and/or other such electronic devices. In various embodiments, a plurality of user devices associated with one or more users may be communicatively coupled to compliance platform 102.

Compliance entities 142 may be electronic devices associated with various entities that include regulations to be complied with. Such compliance entities 142 may include, for example, legal databases of various geographical locations (e.g., municipalities, cities, counties, states, provinces, countries, and/or other geographical locations), insurance entities, regulatory bodies, and/or other such entities that provide for regulations that need to be complied with. In certain embodiments, compliance entities 142 may include electronic devices configured to provide regulatory data.

External auditor 144 may be an auditing body associated with one or more compliance entities. External auditor 144 may be an auditor for such bodies configured to determine whether a user (e.g., healthcare provider) is conforming to the regulation of the associated compliance entity. In various embodiments, external auditor 144 may be configured to access compliance platform 102 to perform such audits. Permission of external auditor 144 to access sensitive data within compliance platform 102 may be controlled by role/permission module 126.

Figure 2:
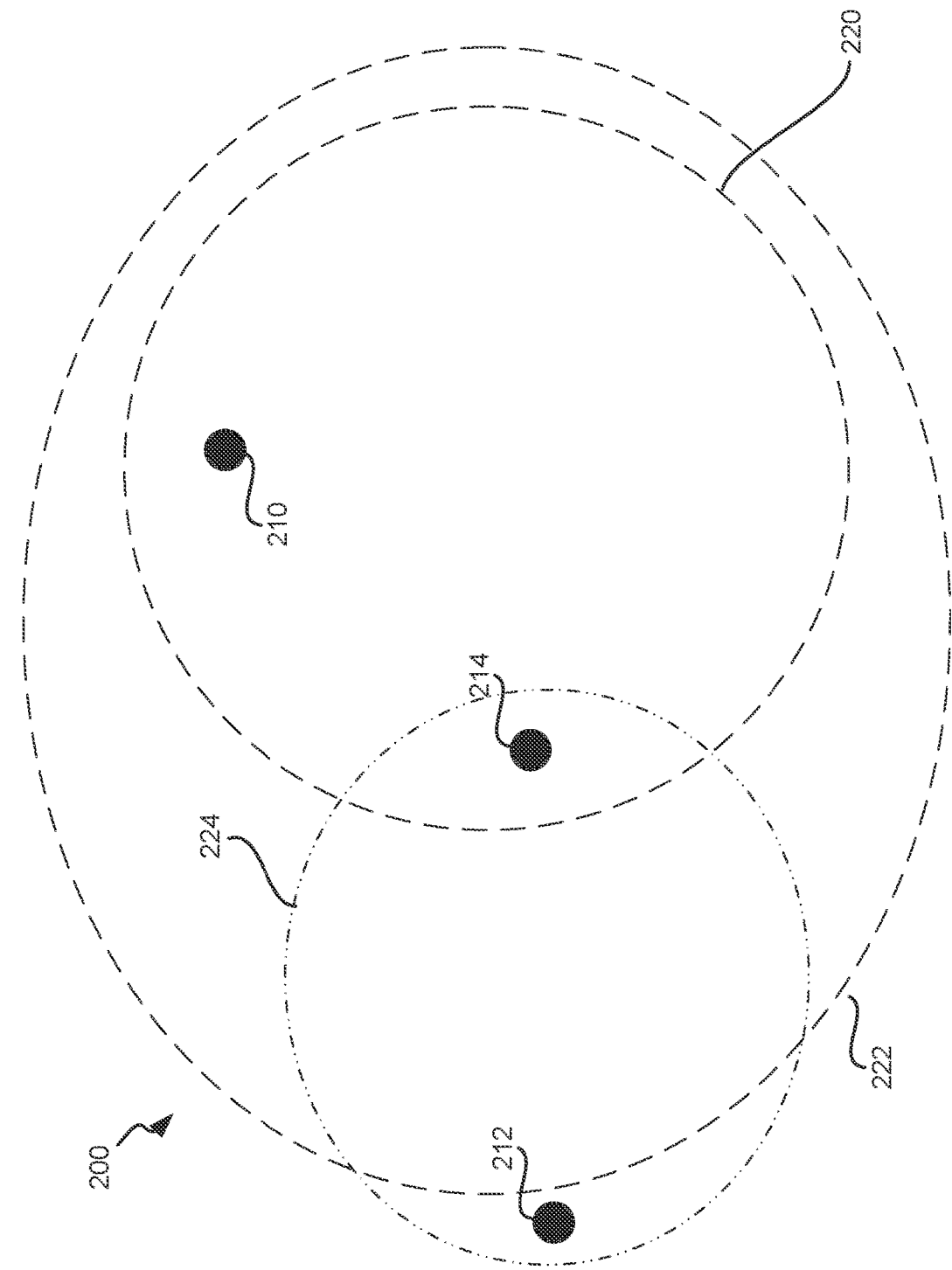
FIG. 2 illustrates an example of geofences for compliance dataflow management, in accordance with some embodiments.

FIG. 2 illustrates an example of geofences for compliance dataflow management, in accordance with some embodiments. FIG. 2 illustrates example 200 that includes users 210, 212, and 214 and geofences 220, 222, and 224.

Users 210, 212, and 214 may be various users requiring compliance with one or more entities (e.g., municipalities, cities, counties, states, provinces, countries, other geographical locations, insurance entities, regulatory bodies, and/or other such entities). Geofences 220, 222, and 224 may be geofences associated with the location of various such entities. Thus, users within such geofences may require compliance with the entities of the associated entities.

The systems and techniques described herein may utilize geofences to determine the entities (e.g., the regulations thereof) that a user needs to comply with. As such, the systems and techniques described herein may erect geofences to denote areas that the various entities cover. As shown in example 200, user 212 is located within geofence 224. Thus, user 212 may be required to only comply with the regulations of the entity of geofence 224. Meanwhile, user 214 is located within the overlapping portions of geofences 220, 222, and 224. Thus, user 214 may be required to comply with the regulations of the entities associated with geofences 220, 222, and 224. User 210 is located within geofences 220 and 222 and, thus, may be required to comply with the regulations of the entity of geofences 220 and 222.

The compliance platform described herein may be configured to determine the location of various users via, at least, geofences. Such geofences may be created by, for example, location module 134 and determined via, for example, location data (e.g., GPS device) received from the user devices. The compliance platform may then automatically determine the regulations of the jurisdictions that need to be complied with from such data and, for example, access the appropriate jurisdiction database, form database, and/or workflow database, accordingly.

Variously, the geofences may be associated with different forms of jurisdictions. Thus, though certain geofences may be associated with geographical jurisdictions (e.g., for compliance with regulations of a location), other geofences may denote the operational boundaries of entities such as insurance entities. Accordingly, geofences may be utilized for determining whether compliance is required with many different types of entities.

Figure 3:
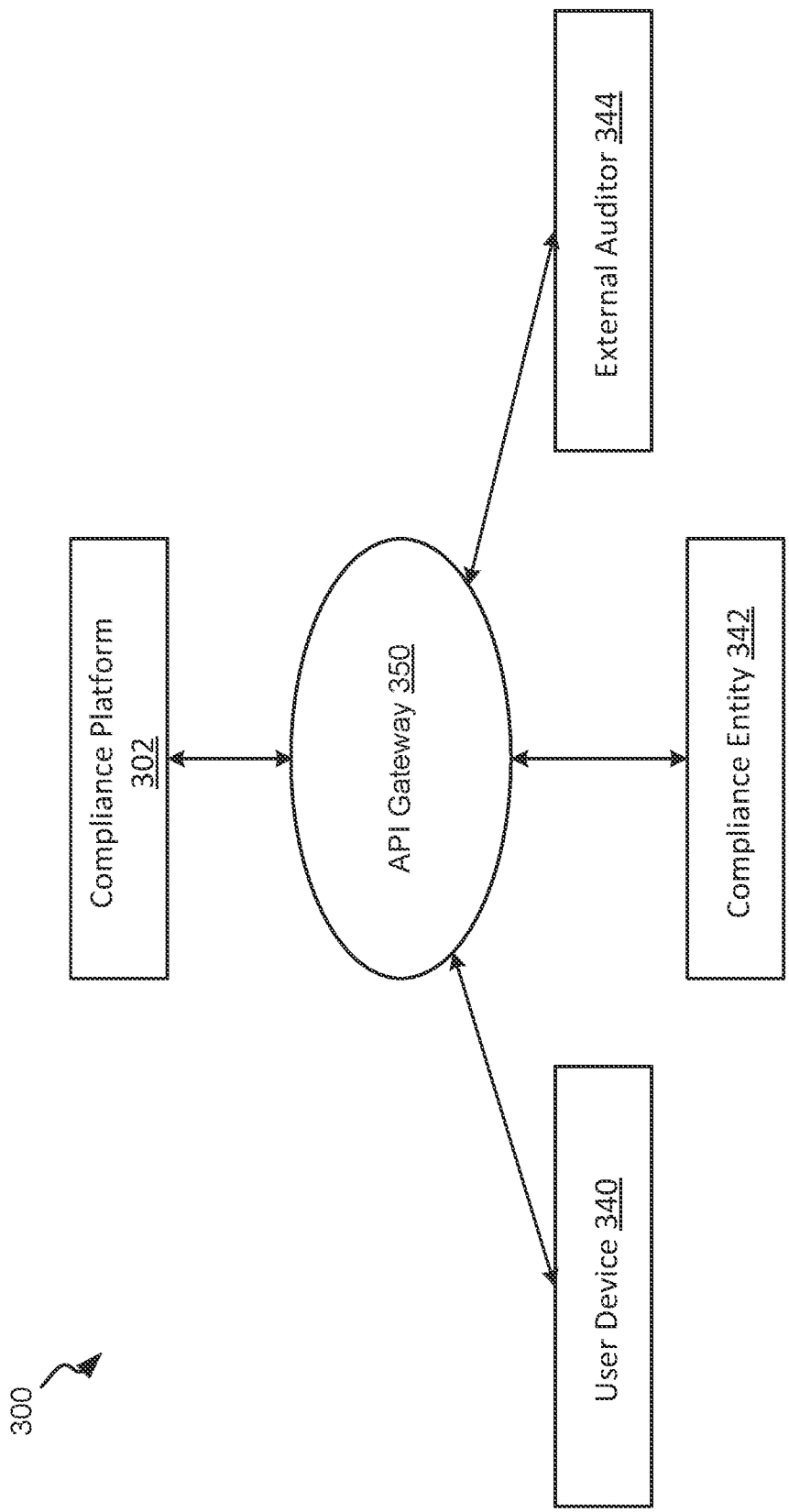
FIG. 3 illustrates a block diagram of another example system for compliance dataflow management, in accordance with some embodiments.

FIG. 3 illustrates a block diagram of another example system for compliance dataflow management, in accordance with some embodiments. FIG. 3 illustrates system 300, which is configured to implement the techniques and processes described herein. System 300 may include compliance platform 302, API gateway 350, user device 340, compliance entity 342, and external auditor 344.

User device 340, compliance entity 342, and external auditor 344 may be as described herein. One or more of user device 340, compliance entity 342, and external auditor 344 may be configured to access the various functions of compliance platform 302 via API gateway 350. Thus, the various techniques of compliance platform 302 may be configured as one or more APIs and API gateway 350 may provide access to the APIs of compliance platform 302. For example, API gateway 350 may receive log-in or authentication credentials from a user of user device 340. API gateway 350 may verify that the requesting entity includes the appropriate authorization to access the requested API. Based such credentials, API gateway 350 may then allow for user device 340 to access an API of compliance platform 302 (e.g., an API allowing for a workflow to be provided to user device 340 to onboard a new patient).

The various systems and techniques described herein may be provided as one or more APIs. Thus, for example, each of the techniques of FIGS. 4-7C may be separate APIs. Furthermore, in certain embodiments, portions of techniques, such as accessing one or more databases, may be separate APIs. Thus, authentication of a user and determination of the access privileges of the user may be provided by one API while physical access to the database may be provided as a separate API. Such a configuration allows for individual techniques described herein, or portions thereof, to be utilized by third parties. Thus, users may comply with the regulations and/or requirements of certain jurisdictions by calling just the APIs related with the action. In certain embodiments, APIs may additionally allow for the verification of licenses of a target (e.g., a compliance workflow may include such verification, and an API may be called to verify the license of the target for compliance, such as a doctor, through access to the appropriate device or database).

FIGS. 4-7C are process flowcharts illustrating portions of compliance dataflow management techniques, in accordance with some embodiments. Each of the techniques of FIGS. 4-7C may be implemented as one or more APIs, according to the techniques described herein.

Figure 4:
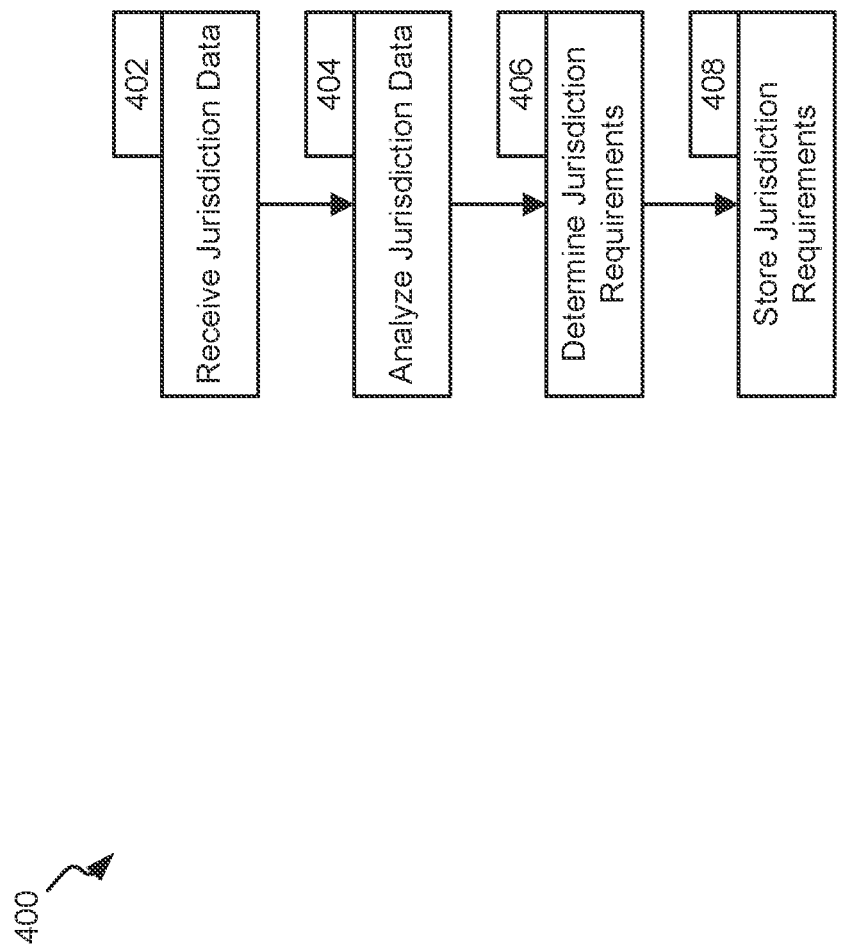
FIGS. 4-7C are process flowcharts illustrating portions of compliance dataflow management techniques, in accordance with some embodiments.

FIG. 4 illustrates technique 400 for interpreting jurisdiction requirements, such as regulations associated with specific jurisdictions. In 402, jurisdiction data may be received (e.g., via one or more communication techniques such as data provided through communication networks). Jurisdiction data may include, for example, rules and regulations associated with a jurisdiction, requirements for reporting for a jurisdiction, updates to the rules, regulations, and/or requirements, commentary and/or interpretation (e.g., updated legal interpretation), and/or other such data. In various embodiments, jurisdiction data may include metadata and/or data configured for consumption by users (e.g., forms that are presented in plain English language).

In 404, jurisdiction data may be analyzed (e.g., by the processor of the compliance platform and/or by a trained compliance personnel). Analysis of the jurisdiction data may include analysis of the natural language of any plain language regulations and/or analysis of the metadata (e.g., via a machine learning module or through an API allowing for conversion of plain language into metadata). In certain embodiments, analysis of the jurisdiction data may include converting natural language of the jurisdiction data into predefined terms (e.g., metadata signifying the natural language may be associated with predefined terms and, thus, the metadata may then be transformed to data indicating the predefined terms). Thus, for example, various jurisdictions may utilize different vocabulary to express the same concept. The compliance platform (e.g., via a machine learning module and/or through metadata conversion as described herein) may convert the various different vocabulary used by jurisdictions to standardized vocabulary. Such a technique allows for the determination of requirements of various jurisdictions and the standardization of the requirements of the various jurisdictions, allowing for requirements to be comparable and for workflows to be generated that may utilize shared forms (e.g., for providing of certain information) between jurisdictions. Conversion may additionally allow for internal audits (e.g., via auditor 124) to be performed across a plurality of different jurisdictions.

In 406, based on the analysis of the jurisdiction data in 404, the jurisdiction requirements are determined. In certain embodiments, the jurisdiction requirements are determined based on the standardized vocabulary provided in 404. Thus, after the jurisdiction requirements are standardized into a consistent format (e.g., used for all regulations within the compliance platform), the requirements are then determined from the jurisdiction data that has been standardized. For example, in certain embodiments, each category of requirements may be associated with an identifier (e.g., a numerical identifier) of a first category. In certain such embodiments, each category may include a plurality of different possible regulations (e.g., based on previous analysis and/or based on machine learning). The different possible regulations may, for example, be associated with an identifier of a second category. The standardized jurisdiction requirements may be standardized according to the identifiers and the requirements may be accordingly determined by analyzing the identifiers.

Determination of requirements from standardized jurisdiction data allows for generation of workflows using standardized forms and/or creation of forms that may be utilized across a plurality of jurisdictions (e.g., with the same or with different workflows), allowing for the conservation of memory and resources, as described herein.

In 408, the jurisdiction requirements that are determined and/or updated in 406 may be stored within the appropriate database. Storage of the jurisdiction requirements may include, for example, storage of forms generated within 406 in the form database and storage of the workflow generated in 406 in the workflow database.

Figure 5:
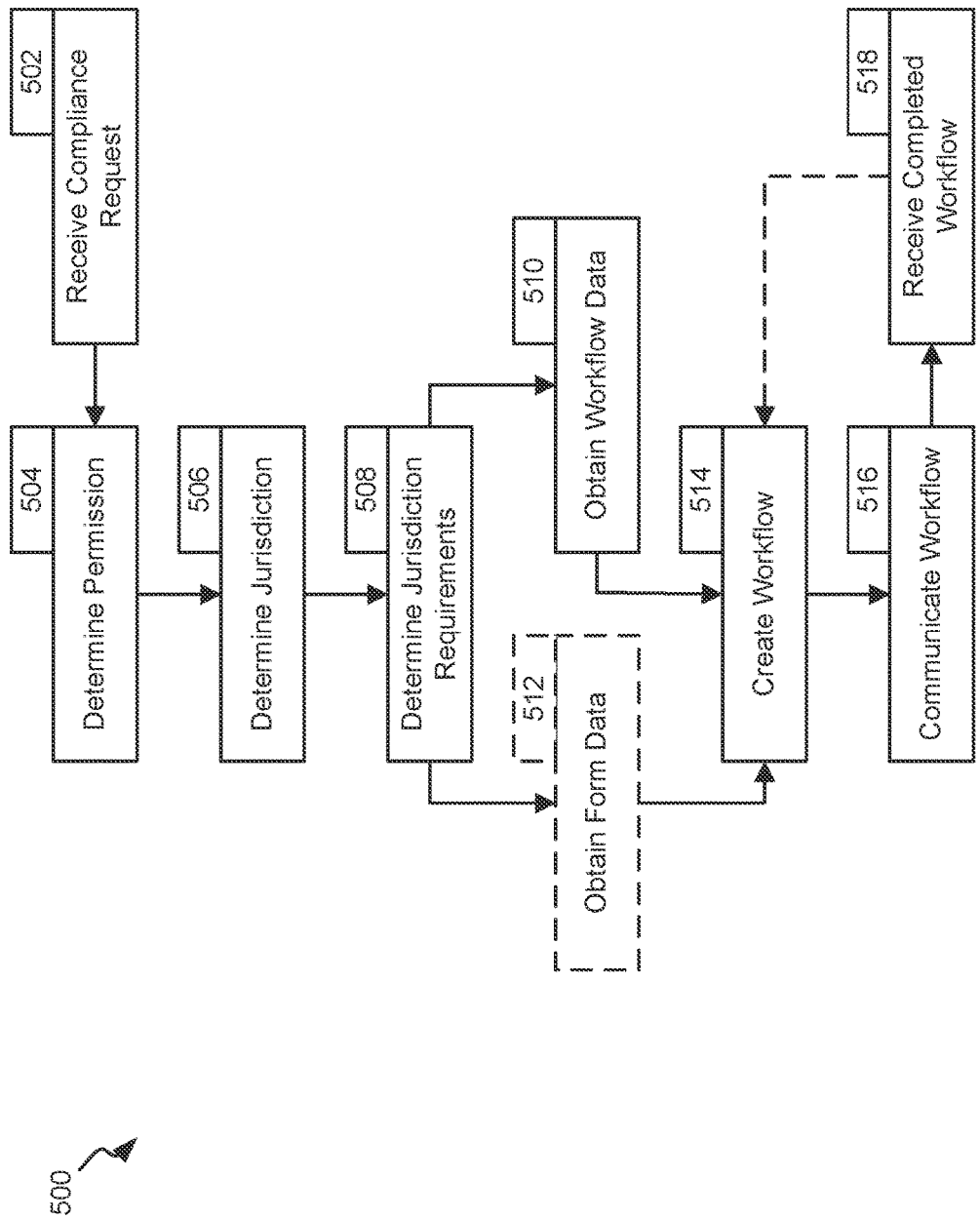

FIG. 5 illustrates technique 500 for the determination of the appropriate form and workflow, based on the appropriate compliance action and jurisdiction. In 502, a compliance request is received. The compliance request may include, for example, a request for compliance with the regulations and/or requirements of one or more jurisdictions. In certain embodiments, the compliance request may include data identifying the requesting party (e.g., the entity and/or the individual), the associated entity, any associated parties (e.g., employees), the compliance subject matter (e.g., the category for compliance), the patient, the healthcare provider (e.g., healthcare providing entity, practitioner, and/or group or individual), any procedures performed, and/or other such information.

Based on the compliance request of 502, the permission of the requesting party may be determined. Permission of the requesting party may be determined from the identity of the requesting party (e.g., the entity and/or the individual) by, for example, role/permission module 126. In various embodiments, various compliance actions may be allowed to be performed only by parties with the appropriate permission level. Such permission levels may be stored in, for example, the returns database. The compliance platform (e.g., role/permission module 126) may, based on the identity of the requesting party and the data stored within the returns database, determine the permission level of the requesting party by accessing the returns database. The permission level of the requesting party may then be utilized to inform the forms that the user is allowed to access.

In 506, based on the jurisdiction and the compliance request (e.g., the request for compliance with the regulations and/or requirements), the jurisdiction requirements may be determined. Thus, for example, the compliance platform may, utilizing the data indicating the jurisdiction and the compliance request, access the jurisdiction database and determine the jurisdiction requirements. The jurisdiction database may be data indicating the requirements of the jurisdiction, as described herein.

Based on the jurisdiction requirements, form data associated with the appropriate form may be obtained from the form database in 512 and workflow data associated with the appropriate workflow may be obtained from the workflow database in 514. In certain embodiments, the compliance request may indicate the subject for compliance (e.g., to comply with insurance regulations). Based on the subject for compliance, the appropriate form and/or workflow may be selected. In various embodiments, the appropriate form may be selected based on the permission level, the jurisdiction, and the compliance request. Thus, the compliance platform may determine the appropriate forms for the compliance request based on the jurisdiction. Thus, for example, certain jurisdictions may require certain forms for a given compliance request. The compliance request may additionally determine the permission level of the requesting party and determine if the requesting party is permitted to obtain the form. The appropriate form may then be accordingly provided.

In various embodiments, the form may be a complete form with highlighted questions (e.g., an existing form). However, in other embodiments, the form may be a determination of the data that is required for compliance (e.g., data related to answers provided by the user, such as whether the subject for compliance is a new hire or an existing employee). In such embodiments, the form determined may be requests for data (e.g., a collection of questions) provided to the user. Accordingly, in such embodiments, form data may not need to be accessed (thus, 512 may be optional). Instead, the requests for data may be determined from, for example, the jurisdiction and/or the workflow data and a workflow determined from the requests for data.

Alternatively, concurrently, or sequentially (e.g., after 512, in an unpictured embodiment), the workflow data associated with the appropriate workflow (e.g., the data required for the given compliance request for the jurisdiction) may be obtained from the workflow database in 510. In certain embodiments, the workflow data may indicate, for example, the responses and/or data that are required to be provided for a given jurisdiction. Thus, the workflow data is selected based on the jurisdiction. In certain such embodiments, the workflow data may be provided independent of the jurisdiction. That is, the workflow data is not connected to specific forms, allowing for the workflow data to modify the form data, as in 514.

The workflow data may be selected based on the permission level, the jurisdiction, and the compliance request. Thus, the appropriate workflow for the compliance request based on the jurisdiction and the compliance request may be selected by the compliance platform. In various embodiments, forms may be shared between a plurality of jurisdictions and/or a plurality of compliance requests. In certain such embodiments, workflows may differentiate the compliance process between the plurality of jurisdictions and/or between different compliance requests. Thus, according to the jurisdiction, the compliance request, and/or the permission level, the appropriate workflow may be selected.

In certain embodiments, workflow data may include the selection and/or provisioning of certain requests for data (e.g., questionnaires) beyond that associated with stored forms. Such data may, for example, be provided to the user to establish background for the result (e.g., for the field of compliance, for the type of compliance needed, and/or for other background information). Based on such data, the appropriate form, in 512, may be selected and/or the appropriate workflow, in 514, may be generated.

In certain embodiments, jurisdictions requirements may first be determined in 508, based on the compliance request and the jurisdiction, as well as permission levels. Data within the jurisdiction database may then indicate 1) the appropriate form for the compliance request and/or 2) the appropriate workflow for the compliance request. As such, data within the jurisdiction database may identify the data to be accessed from the form database and/or the workflow database. Based on the identification, the appropriate form from the form database and the workflow database is accordingly accessed. In another embodiment, the jurisdiction data and/or the workflow data may allow for a determination of the appropriate requests for data to be provided to the user.

The form data and the workflow data may be combined in 514 to create the appropriate workflow. Thus, the form associated with the form data may include a plurality of portions for the user to provide data. Based on the jurisdiction and the compliance request, one, some, or all of those portions may be required to be provided with data from the user (e.g., filled out by the user). The compliance platform determines such sections based on the workflow data. That is, the workflow data may inform what data is required, based on the jurisdiction and compliance request. The compliance platform may then determine the portions of the form that would be provided with data from the user, based on the workflow data. Additionally or alternatively, the form data may be a uniquely created form (e.g., not a form provided by the jurisdiction and, instead, determined by the compliance platform). Such form data may be for forms that are specifically created for various compliance scenarios. In other embodiments, a request for data (e.g., questionnaires) may be determined from workflow data and/or jurisdiction data. A complete workflow for compliance may be accordingly created.

In certain embodiments, such as embodiments where the form is requests for data (e.g., a collection of questions) provided to the user, the workflow may be one or more discrete questions provided to the user. The user may provide responses to such requests. In certain such embodiments, the workflow may be a plurality of requests for data and subsequent requests may be dependent on responses to the previous requests. As such, the workflow may be a branching workflow. Based on the responses to the requests, the data may be stored within the databases of the platform, and/or one or more forms may be generated/filled out by the platform, based on the responses to the request for data.

In certain embodiments, the workflow created in 514 may be analyzed by, for example, compliance module 130. Such analysis may determine whether the workflow created is compliant with the regulations and/or requirements of the jurisdiction. In various examples, the workflow created may be based on a combination of form data and workflow data separately stored; determining compliance after the creation of the complete workflow may, thus, allow for a determination of whether the combination of the form data and the workflow data results in a complete workflow that meets requirements.

In certain embodiments, the complete workflow may be branching (e.g., the workflow data may indicate branching choices). That is, the workflow may include a plurality of steps (e.g., requests for data, which may be questions in a questionnaire) and, based on the user response to a first step, a second step or a separate third step (e.g., subsequent requests for data, which may be follow-on questions in a questionnaire) may be selected. Such branching workflows may be appropriate situations where data required for compliance is based on a plurality of possible responses given by a respondent.

For branching workflows, data provided by the user may be communicated to the platform for each step or the completed workflow may be communicated as one dataset. In embodiments where data is provided by the user to the platform for each step, machine learning may be utilized to determine whether user responses are indicative of user anomalies or pitfalls (e.g., indications that the user is confused and is misunderstanding the question and/or workflow). Machine learning module may be trained to determine when a user response typically indicates user anomalies or pitfalls (e.g., a user providing an age that is biologically improbable) and, upon such a determination, provide feedback to the user to try to correct the user misunderstanding.

The workflow may then be communicated (e.g., to a user device) in 516. Communication of the workflow may be according to the techniques described herein and may include communicating data, such as a combined workflow that includes sections for filling out by the user, via the communications networks described herein.

Completed workflow data responses may be received in 518. In various embodiments, the completed workflow data may be data received in one batch (e.g., a fully completed questionnaire) or may be data received at a plurality of different periods of time. Thus, for example, a first request may be communicated and a response provided (e.g., a response to a question of, "Is the subject a full-time employee?") and, based on the response provided, subsequent follow-up requests may be communicated and responses received (e.g., if the response is "No", a follow-up request may ask "How much is the employee paid per hour?"). Accordingly, in certain embodiments, 514 to 518 may be repeatedly performed until all data required is obtained. Thus, for example, a portion of a branching workflow may be created in 514 and communicated to the user in 516. Based on the data provided by the user in reply in 518, an additional portion of the branching workflow may be created when the technique returns to 514. Such an additional portion may be an additional request for data that is based on previous response received. Accordingly, branching workflows may be created and/or modified based on responses received by the user. Such data may be, for example, generated by the platform, communicated via networks as described herein to the user, responses received by the platform via the network from the user, and further workflow portions determined and communicated by the platform.

In certain other embodiments, a full branching workflow may be communicated to the user. Thus, a workflow with all possible branching paths may first be created in 514 and communicated to the user in 516. The user may then provide responses within the workflow and the workflow may select follow on questions based on the responses received. After completion of the workflow, the full collection of responses may be provided to the compliance platform. In certain such embodiments, 514 to 518 may not be iterated and, thus, the full workflow may be generated in 514 before communication to the user.

In various embodiments, the responses may be provided as user selections of possible answers and/or as text. Text responses may be analyzed through natural language recognition software and a response accordingly determined.

Various embodiments of technique 500 thus divides access of the form data and the workflow data. Such a technique allows for the form data and the workflow data to be stored within separate databases. Furthermore, such a technique allows for the form data to be shared, conserving resources as described herein, and allows for the form data and the workflow data to be separately updated. In certain embodiments, the workflow data may be metadata. Updates to regulations and/or requirements may result in the updating of workflow data without updating of form data. As such, only metadata may be required to be updated based on updates in regulations, further saving memory and processing resources. Additionally, the storage of form data and workflow data separately from each other increases security, as form data or workflow data may each separately not provide a useful information.

Certain such embodiments of technique 500 requires the combining of workflow data with form data to create a useable workflow. As the workflow data is consistently being updated, the creation of a workflow for each compliance action prevents the usage of out of date workflows, increasing the accuracy of compliance. Furthermore, the compliance platform is able to detect outdated form data if up to date workflow data is not compatible with the outdated form data, allowing for detection of out of date forms and the subsequent updating of such forms.

In other embodiments of technique 500, workflows may be determined that may not be tied with specific forms. Such workflows may request data from the user and determine compliance from the reply data. In certain such embodiments, the workflows may be branching workflows. In additional such embodiments, the appropriate form needed for compliance may be selected from the reply data and filled out, while other embodiments may store the reply data as storage of such reply data may be what is needed for compliance.

Technique 500, involving the access of a plurality of different databases to create a workflow for compliance, allows for the sharing of forms across a plurality of jurisdictions and for the updating of requirements, as described herein. Furthermore, such a configuration allows for improved data security as appropriate workflows are generated based on a combination of data from a plurality of databases, instead of access to one database, rendering spoofing of workflows (e.g., for the purposes of fraud) difficult. Such anti-fraud techniques may additionally include metadata from a plurality of the jurisdiction database, the form database, and the workflow database to be present within the completed workflow (e.g., identifying the datapoints of access within each respective database). A user device receiving a completed workflow and/or the compliance platform receiving a filled out workflow may then utilize such datapoints to cross-reference the authenticity of the workflow, to prevent fraudulent workflows from being communicated that would then illicitly steal compliance data (e.g., as described in technique 600).

Figure 6:
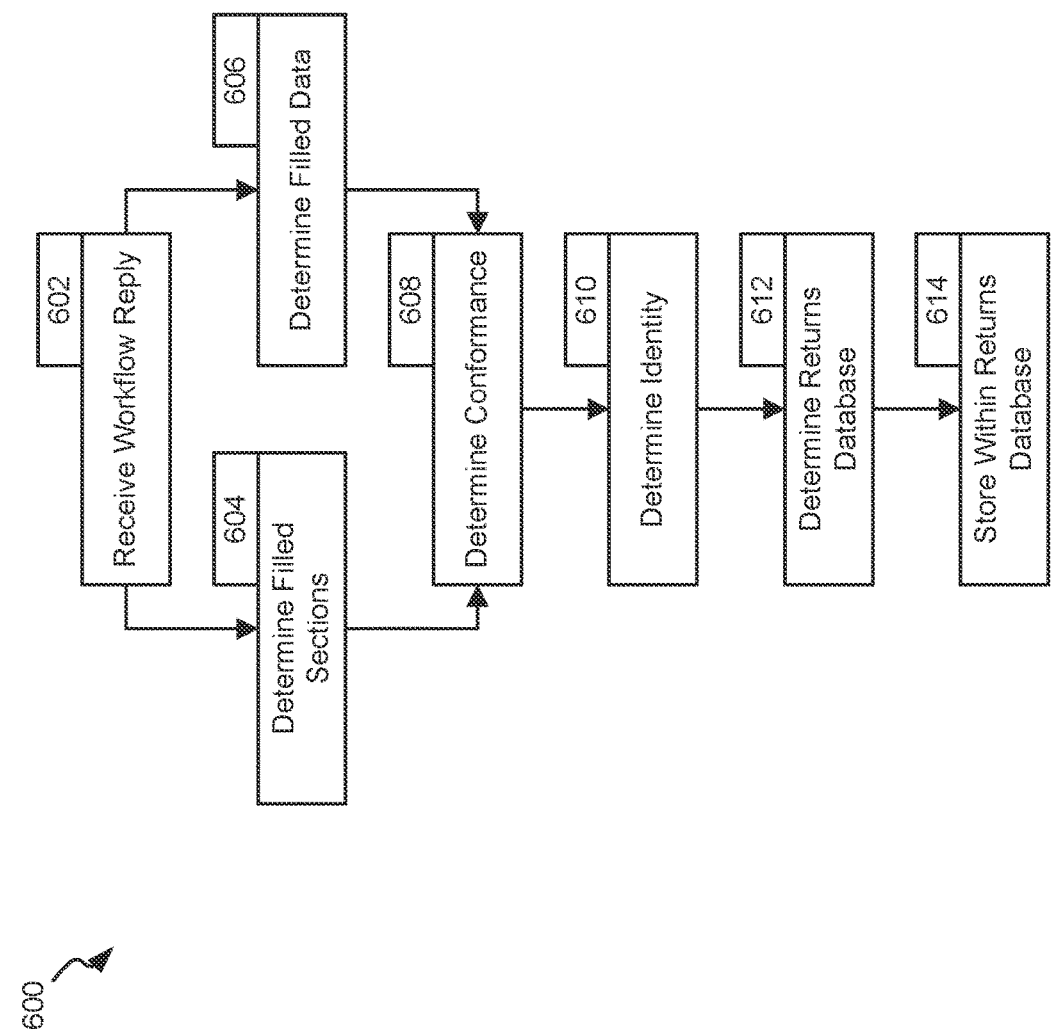

FIG. 6 illustrates technique 600 for processing user replies to workflows (e.g., workflows communicated in technique 500). The workflow reply may be received in 602. Such a reply may be received from, for example, a user device of the user. Thus, the user may fill the portions of the form indicated within a workflow. The filled form may then be communicated to and received by the compliance platform.

In 604, the compliance platform may determine the portions of the workflow that is filled out in 604 and/or determining that the reply data includes appropriate responses to the requests for data. Determining that the filled-out sections includes determining, based on the communicated workflow, whether sections that need to be filled out are actually filled out. For example, in certain embodiments, the workflow may include required and/or optional sections. Such workflow may be associated with the specific patient and/or user and may be stored within, for example, the returns database. The compliance platform, upon receipt of the completed workflow, may then access the returns database and determine if the required sections have been filled out (e.g., data provided by the user). Similarly, requests for data may include required or optional sections and a determination that the appropriate reply data has been provided includes determining that reply data in response to the required requests have been provided.

Sequentially or separately, the filled data may be determined in 606. The compliance platform may identify the filled data within the workflow reply and determine the contents the filled data. In certain such embodiments, analysis of the reply data may also be performed to determine if the reply data is of the valid format (e.g., a request for age may include a determination that the reply data is in a numerical format). In various embodiments, the compliance platform may analyze the filled data and convert the data to a standardized form, similar to techniques utilized for processing regulation updates, standardizing the language of regulations or requirements, or for determining stored data (e.g., with numerical identifiers), as described herein. The compliance platform may analyze the filled data and determine whether the filled data is of the type of data that is in conformance with regulations and/or consistent with the sections (e.g., a determination may be made as to whether a date of birth section includes data indicating a date of birth, instead of indicating other types of data).

Based on determining if the required sections are filled and the data provided, conformance to the regulations of the jurisdictions may be determined in 608. Thus, determination may be made that the sections that are required to be filled are in conformance with regulations (e.g., that no sections that are required have been missed within the workflow). A determination may also be made that the filled data is data that is valid for the sections and, accordingly, meets the rules, requirements, and/or regulations (e.g., that a patient name section includes an actual name of the patient).

In certain embodiments, an authenticity of the received response may also be determined. For example, the workflow may include metadata from each of the plurality of databases accessed to create the workflow provided to the user (e.g., the jurisdiction database, the form database, and the workflow database). The presence of such metadata may be checked and verified. Accordingly, jurisdiction metadata may be present within the workflow identifying the jurisdiction, as stored within the jurisdiction database (e.g., the metadata be a number assigned to the jurisdiction within the jurisdiction database). The metadata may be confirmed to authenticate the received workflow. Metadata associated with the other databases (e.g., data identifying the form used and the workflow accessed) may also be confirmed with the respective database to authenticate the received completed workflow.

Concurrent or consecutive to 608, an identity associated with the workflow may be determined in 610. The identity may be, for example, a name of the patient, a name of the entity requesting compliance, and/or an identity of another party. Based on the identity of the party, the appropriate returns database and/or portion of the database for storage of the workflow replay may be determined in 612 and the workflow reply may be stored in the determined returns database in 614.

Figure 7A:
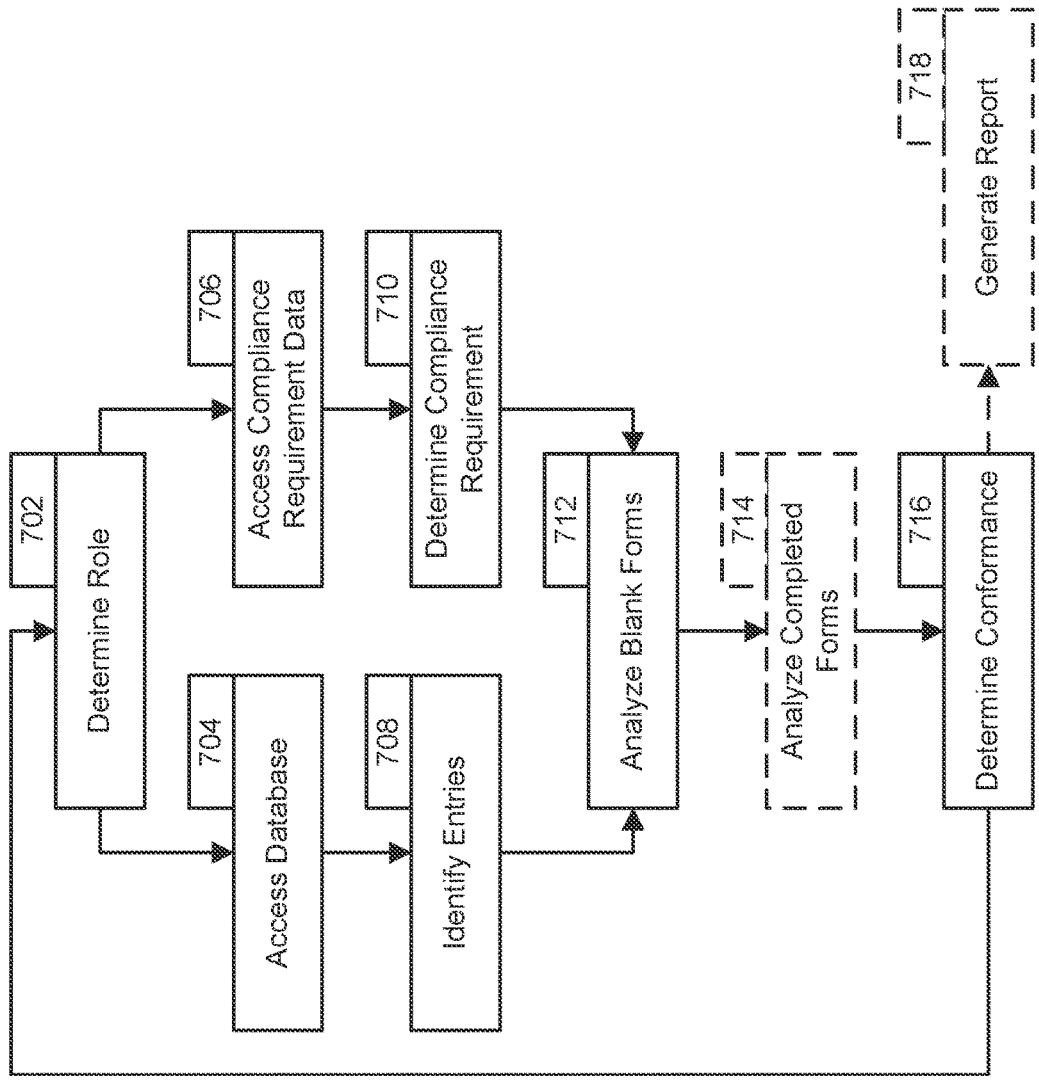

FIG. 7A illustrates technique 700A for automated auditing of the compliance platform. In various embodiments, the automated auditing may be performed by an external auditor or an auditor internal to the compliance platform (e.g., auditor 124). For such internal auditors, audits may be periodically performed (e.g., performed once every half hour, every hour, every half day, every day, every week, every month, and/or periodically performed within another such regular time period) within compliance platform to verify conformance to the regulations of various jurisdictions that an entity is associated with. Other embodiments may perform audits upon instruction or request (e.g., a user associated with the compliance entity may request that an audit be performed).

In 702, a role for the auditor may be determined. The role may indicate the permission level of the auditor and, thus, the security level of documents that the auditor is permitted to access. For example, as certain documents within the returns database may include sensitive information, the role of the auditor (e.g., the permission level) may determine whether the auditor is permitted to access such sensitive documents. In various embodiments, determining the role may also include determining the specific compliance workflow to be audited. For example, the compliance platform may include workflows for compliance with a plurality of different regulations or requirements. Determination of the compliance workflow to be audited allows for the audit to be concentrated on specific subject matter.

Based on the role and/or permission level of the auditor, the appropriate databases may be accessed for auditing in 704. Accordingly, any database such as the jurisdiction database, the form database, the workflow database, and/or the returns database may be accessed for auditing. The auditor may, thus, obtain the corresponding data from the appropriate database. Based on the permission level of the auditor, only a portion of such databases may be accessed, or all of the databases may be accessed (if permission allows). In various embodiments, at least certain returns data, form data, and/or workflow data may be accessed in 704. In certain embodiments, the auditor may first access the jurisdiction database to determine the form and/or workflow data associated with the regulations and/or requirements of a subject matter associated with a jurisdiction. The jurisdiction data may identify the appropriate form and/or workflow data and the auditor may then access the form database and the workflow database to audit such data.

In 708, based on the form data and the workflow data, the entries of a specific workflow are determined. Such specific workflows may be, for example, the compliance workflows identified in 702. Identifying the entries may include identifying the portions of the form to be filled out based on the workflow. The type of data to be provided may, accordingly, be identified.

In 706, compliance requirement data may be accessed. The compliance requirement data may be, for example, jurisdiction data indicating the type of data to be provided to be in compliance with the jurisdiction for a given compliance subject matter. Based on such data, the compliance requirement for the jurisdiction may be determined in 710. Thus, the auditor may determine the subject matter of the compliance and the jurisdiction associated with the compliance and access the jurisdiction database for the appropriate jurisdiction data associated with the subject matter of the compliance and the jurisdiction. Based on the jurisdiction data, the auditor may then determine the requirements (e.g., data requirements) for compliance within the jurisdiction.

In 712, the auditor may analyze blank forms to determine if workflows provided to users are in compliance with the regulations and/or requirements. The auditor may accordingly utilize the form data and workflow data received to determine (e.g., recreate) the workflow that is provided to users (e.g., in 708). The compliance requirements determined in 710 may then be used to analyze the blank (e.g., without filled out data) workflows that are provided for users. A determination may be made as to whether the blank workflow includes sections for filling out where, if a user where to provide the requested information, the workflow would comply with the requirements of the regulation and/or requirements of the jurisdiction.

In certain embodiments, the auditor may not be granted permission to access the appropriate form or workflow. In such a situation, the auditor is unable to determine the completed workflow as the auditor is missing at least a portion of the data needed to recreate the workflow.

Reply data from the returns database may be analyzed in optional 714. Whether the auditor is permitted to analyze the patient data may be based on, for example, the permission level of the auditor (e.g., determined in 702). As the patient data may include sensitive data, the auditor permission level may be determined to include access to such sensitive information before the auditor is allowed to analyze the patient data.

If the auditor is allowed to analyze such reply data, the auditor may, from the completed forms and/or reports of the reply data, determine whether one or more of the completed forms are in compliance with the regulations and/or requirements of the jurisdiction.

Such reports and/or completed forms may include various standardized and/or entity specific reports and/or determinations. The reports and/or determinations may be directed to compliance that may include, but are not limited to, determinations and/or reports associated with municipal, county, state, and/or federal entities, as well as reports from The Joint Commission (TJC), Commission on Accreditation of Rehabilitation Facilities (CARF), and/or other accrediting agencies as described herein.

Thus, for example, various reports and/or determinations may include risk management reports, credentialing reports, one or more required competency reports (which may include various frequencies for providing, which may be determined by one or more state, TJC, and/or internal policies), human resources documentation reports (based on frequencies determined by state, TJC, and/or internal policies), training reports (based on frequencies determined by State, TJC, and/or internal policies), Expiring License and Primary Source Verification Reports, Expiring Contracts/Agreements Reports, Expiring Continuing Education Unit (CEU) Report, and/or reports of any incomplete tasks. TJC reports may include, for example, Infection Prevention & Control Compliance Report, National Patient Safety Goal Compliance Report, Environment of Care Compliance Report, Emergency Management Compliance Report, Leadership Compliance Report, Medication Management Compliance Report, Performance Improvement Compliance Report, Waived Testing Compliance Report, and Information Management Compliance Report. CARF reports may include, for example, Leadership & Governance Compliance Report, Risk Management Report, Health and Safety Compliance Report, Performance Improvement Compliance Report, and Program Standards Compliance Report. In various other embodiments, jurisdiction database 104 and/or form database 106 may include a library of regulations and/or standards. Such regulations and/or standards may be associated with and/or determined from data directed to policies and/or supporting documentation (e.g., stored within jurisdiction database 104 and/or form database 106).

The reports may allow for the determination of whether one, some, or all of the completed forms indicate that the entity in is compliance (e.g., with the regulations and/or requirements of the jurisdiction). Such a determination may include, for example, whether the data within the finished workflow includes data provided (e.g., within the format required) for all portions of the workflow where data is required to be in compliance within the jurisdiction. The determination may additionally include a determination of whether the data provided and/or stored (e.g., the substance of the data) is in compliance with the regulations and/or requirements of the jurisdiction. As such, for example, various responses provided may be converted to standardized language (e.g., according to the techniques described herein) and the standardized language may then be analyzed to determine whether the response conforms with the rules and regulations of the jurisdiction. Certain workflow responses, such as names, may not be converted into standardized formats.

In certain embodiments, patient data may be stored as metadata requiring the workflow data and the form data to analyze (e.g., to create a completed form for auditing). In certain such embodiments, the auditor may not be granted permission to access the appropriate form or workflow. The auditor may, in error, be able to access the returns data. Nonetheless, in such a situation, the auditor is unable to determine the completed form for audit as the auditor is missing at least a portion of the data needed to recreate the workflow. Returns data is thus protected from audit despite the error.

Based on the analysis of the blank forms and/or the completed forms, conformance with the regulations and/or the requirements may be determined in 716. Non-conformance may also be determined. In certain embodiments, if conforming, data may be provided (e.g., to a user device) indicating conformance, but other embodiments may not generate any data based on a determination of conformance. In certain other embodiments, a compliance score may be determined based on the conformance and non-conformance. The compliance score may include a plurality of different components. For example, the components may include a score for the forms used and a score for the workflow used. If non-conformance is determined, data may be provided to a user device indicating non-conformance and, in certain embodiments, highlighting the areas of non-conformance. In certain embodiments, non-conformance may be fixed by the compliance platform, if solutions are determined.

In certain embodiments, the systems and techniques described herein include reports generated by, for example, compliance module 130 and/or auditor 124. Thus, in optional 718, such a report may be generated. The report may aggregate compliance data points from one or more forms, documents, surveys, reports, and/or other items (e.g., completed surveys or data available from third party sources, such as government data associated with the entity) to generate a complete report indicating compliance status across various areas of compliance. Such areas of compliance may include, but are not limited to reports from municipal, county, state, and/or federal entities, as well as reports from The Joint Commission (TJC), Commission on Accreditation of Rehabilitation Facilities (CARF), and/or other accrediting agencies as described herein. The reports may include various reports described herein.

The report may provide an overall compliance score and/or may indicate compliance of certain categories or subjects. In certain embodiments, the report may be generated based on, at least in part, the conformance determined in 716. Additionally or alternatively, various systems and/or components described herein may access the reports and other data stored and associated with the entity and the report may be generated, at least in part, based on such reports and/or other data. Thus, for example, a determination may be made from the reports and other data as to compliance and/or conformance of the entity for various subjects.

The report may indicate areas of conformance and/or non-conformance as well as possible options to become compliant. In certain embodiments, the report may be variously provided to the entity, to regulating bodies, and/or to other parties (e.g., an external auditor).

In various embodiments, technique 700A may periodically repeat.

Figure 7B:
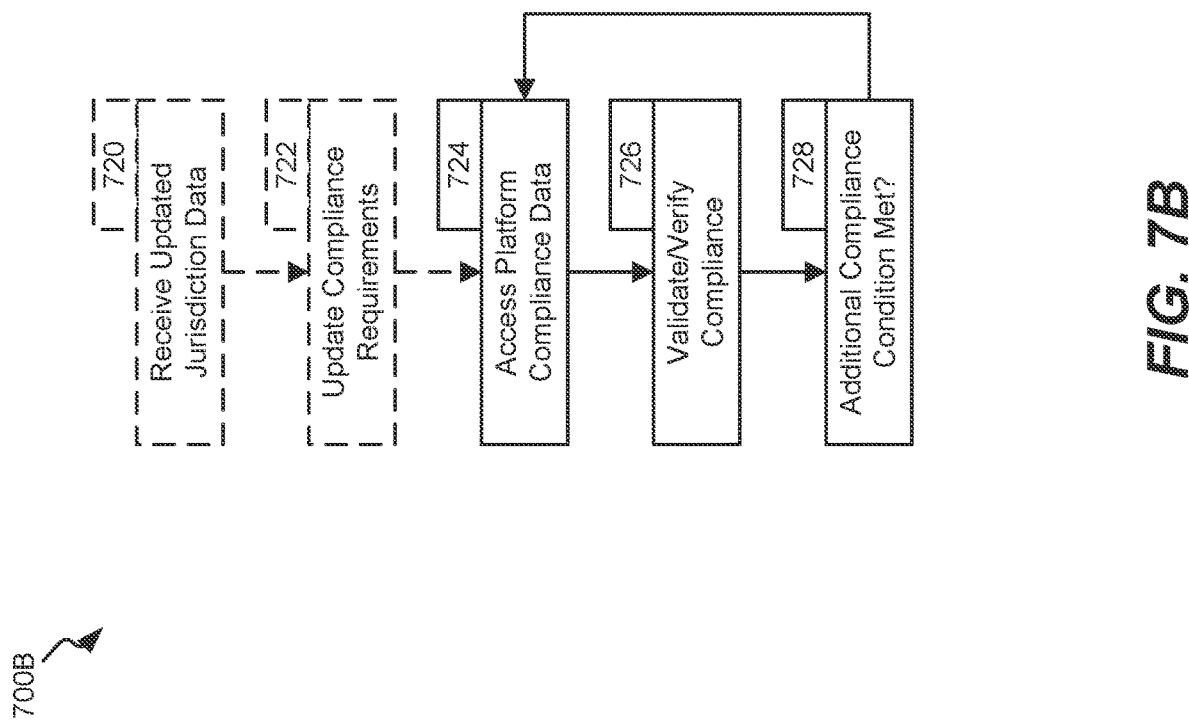

FIG. 7B illustrates technique 700B for automated compliance validation. FIG. 7B illustrates technique 700B that may determine, from data provided by a user or organization, if that user or entity is in compliance with the rules and regulations of a jurisdiction. In certain such embodiments, portions of technique 700B may be performed by, for example, an automated auditor of the platform.

In various embodiments, such auditing may be auditing of data provided by the user on an one-time, periodic, or continuous basis. Thus, for example, responses to data requests may be received by the platform as to various aspect of a user's or entity's human resources practices. Such response data may, when received, be analyzed to determine if the user and/or entity is in compliance with the relevant labor laws of a jurisdiction. Furthermore, such response data may be stored within the appropriate database. The data may be periodically analyzed (e.g., based on time elapsed since last analysis, due to changes in relevant rules and regulations, and/or based on other conditions) and determination may be made during each of these analysis as to whether the data indicates that the user and/or entity is currently in compliance. Based on the analysis, communications may be provided to the user/entity as to the compliance status.

In optional 720, jurisdiction data may be received. Such jurisdiction data may be data indicating updated rules, regulations, requirements, and/or other aspects of compliance for the subject matter within the jurisdiction. Such jurisdiction data may be similar to jurisdiction data as described herein.

In optional 722, the updated jurisdiction data received may be used to determine updated compliance requirements for the jurisdiction. The updated compliance requirements may be determined according to the techniques described herein for determining compliance requirements.

In 724, the platform's compliance data may be accessed. Such compliance data may include form data, jurisdiction data, location data, and/or other types of data as described herein. Access of such compliance data may allow for the determining of current (e.g., at the time of access) compliance requirements for the jurisdiction and/or subject matter.

In 726, compliance of the user and/or entity for the jurisdiction and/or subject matter may be validated and/or verified (e.g., based on the determined compliance requirements and the returns data). Validation of compliance may be performed on data that has just been received from the user and/or entity and/or on data of the user and/or entity that is stored within the appropriate database. As such, validation may be performed at receipt of data provided by the user, periodically (e.g., once every day, week, month, or another timeframe), and/or if certain conditions are met (e.g., if updated jurisdiction data has been received).

Variously, in 724, requirements for compliance may be established. Such requirements may, for example, include categories of data that must be received from the user, reply data that is acceptable for compliance, a timeframe where compliance is valid (e.g., such data may need to be provided within a certain timeframe, such as one month prior), and/or other such requirements. In 726, such requirements may be validated and/or verified by the platform to determine whether the user and/or entity is in compliance. As such, for example, validation/verification may include determining whether all categories or required data have been provided by the user/entity, whether the reply data received and/or stored from the user/entity is acceptable for compliance and/or indicates a type of data that is acceptable for meeting compliance (e.g., the answers to the questionnaires provided by the user indicates that the entity is in compliance such as, by providing the required yes or no answers, providing answer ranges within an acceptable range of answers, such as through numerical answers, by indicating that certain actions have been performed, and/or through other data provided), whether the reply data was provided within an acceptable timeframe (e.g., whether the data was provided has expired or not), and/or other such techniques.

In certain embodiments, if it is determined that the user/entity is out of compliance and/or about to be out of compliance (e.g., if stored data is about to expire), additional data may be communicated to the user. Such data may indicate non-compliance or imminent non-compliance of the user/entity, include a request for further data from the user/entity (whereas proper reply data would bring the user/entity back into compliance), indicate to the user/entity ways to be in compliance (e.g., the actions required and/or data to be provided in order to be back in compliance), and/or request action from the user/entity in another such manner. As such, technique 700B, upon a determination of non-compliance and/or imminent non-compliance, may provide data indicating actions and/or requirements to the user/entity that may bring the user/entity back into compliance for the subject matter and jurisdiction.

In certain embodiments, distinction may be made between data that is required for compliance versus data that is optional for compliance. For example, certain types of data may be required to be provided/stored in order for a user/entity to be in compliance. Additionally, such types of data may need to be of a certain nature (e.g., answered in a certain manner or within a certain threshold) in order for the user/entity to be in compliance. Other types of data may be optional and may not be required for compliance (e.g., in certain embodiments, providing of such data may result in a requirement that such data may need to be in a certain range in order to be in compliance). The platform may distinguish between data that is required and data that is optional in the validation/verification. In various embodiments, certain platforms may only analyze required data, while other embodiments may analyze both required and optional data. Feedback provided to the user/entity may also only concern required data in certain embodiments (e.g., the feedback may only highlight data that is required for compliance), but may concern both required and optional data in other embodiments (e.g., the feedback may indicate that certain optional data is missing, but that such data is optional).

In 728, the compliance platform may determine whether additional compliance condition has been met to, for example, determine if the user/entity is still in compliance. As such, the additional compliance condition triggers a further round of validation/verification of the compliance of the user/entity. Such a technique may include, for example, a determination of whether time elapsed indicates that an additional round of validation/verification is required, that updated jurisdiction data indicates that an additional round of validation/verification is required, that an additional round of validation/verification has been ordered (e.g., by the user), and/or that another such condition has been met. If such a condition is met, the technique may return to 724 and perform such a validation technique. Thus, it is appreciated that, in various embodiments, some or all of technique 700B (e.g., 724 to 728) may be periodically performed.

Figure 7C:
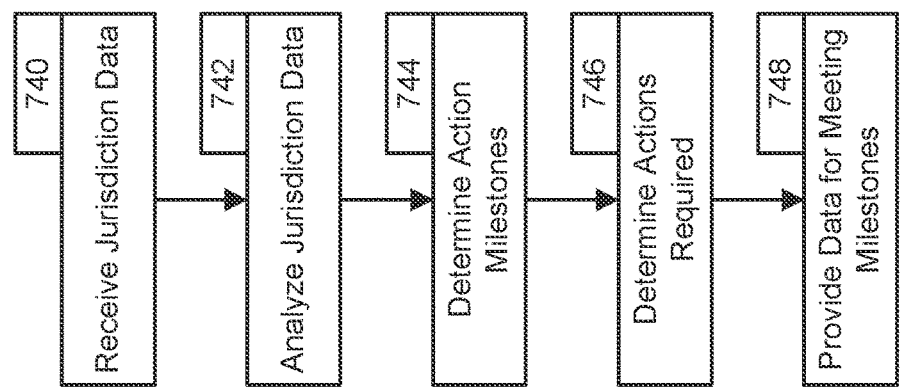

FIG. 7C illustrates technique 700C for automated compliance milestone determination. Such milestones of technique 700C may include, for example, milestones where user/entity action is required. In certain such embodiments, such milestones may be milestones to keep a user/entity in compliance with the rules, regulations, and/or requirements of a jurisdiction. Thus, for example, certain jurisdictions may require yearly fire drills, and technique 700C may aid in a user/entity in performing such fire drills.

In 740, jurisdiction data may be received. The jurisdiction data may be as described herein. The jurisdiction data may be analyzed in 742, according to the techniques described herein. Based on the analysis of the jurisdiction data in 742, a determination may be made in 744 that one or more action milestones are upcoming. Thus, for example, analysis of the jurisdiction data may determine the requirement for a yearly fire drill for each office, bi-yearly sexual harassment training for every employee, and/or every 3 year continuing education training for each professionally licensed employee.

Based on the determination of action milestones in 744, returns data from the returns database may be accessed and a determination made as to the actions required to be in compliance, in 746. Data associated with such actions may be accordingly provided in 748.

Such actions may be based on returns data stored within a returns database. Thus, for example, if returns data indicates that an office just performed a fire drill a week ago, no action may be required. However, if a determination is made that it has been 50 weeks since a fire drill has been performed, a reminder may be generated and provided to the user/entity. If a determination is made that the office is overdue for a fire drill, an urgent reminder may be generated and provided to the user/entity. In certain embodiments, such communications may be scheduled for the future (if there is still time remaining for compliance) or may be provided as soon as possible. In various embodiments, where the action may pertain to only certain members (e.g., employees) of an entity (e.g., based on their role and/or based on data indicating that they are not currently in compliance), such data may identify the members of the organization for which such actions are required.

Figure 8:
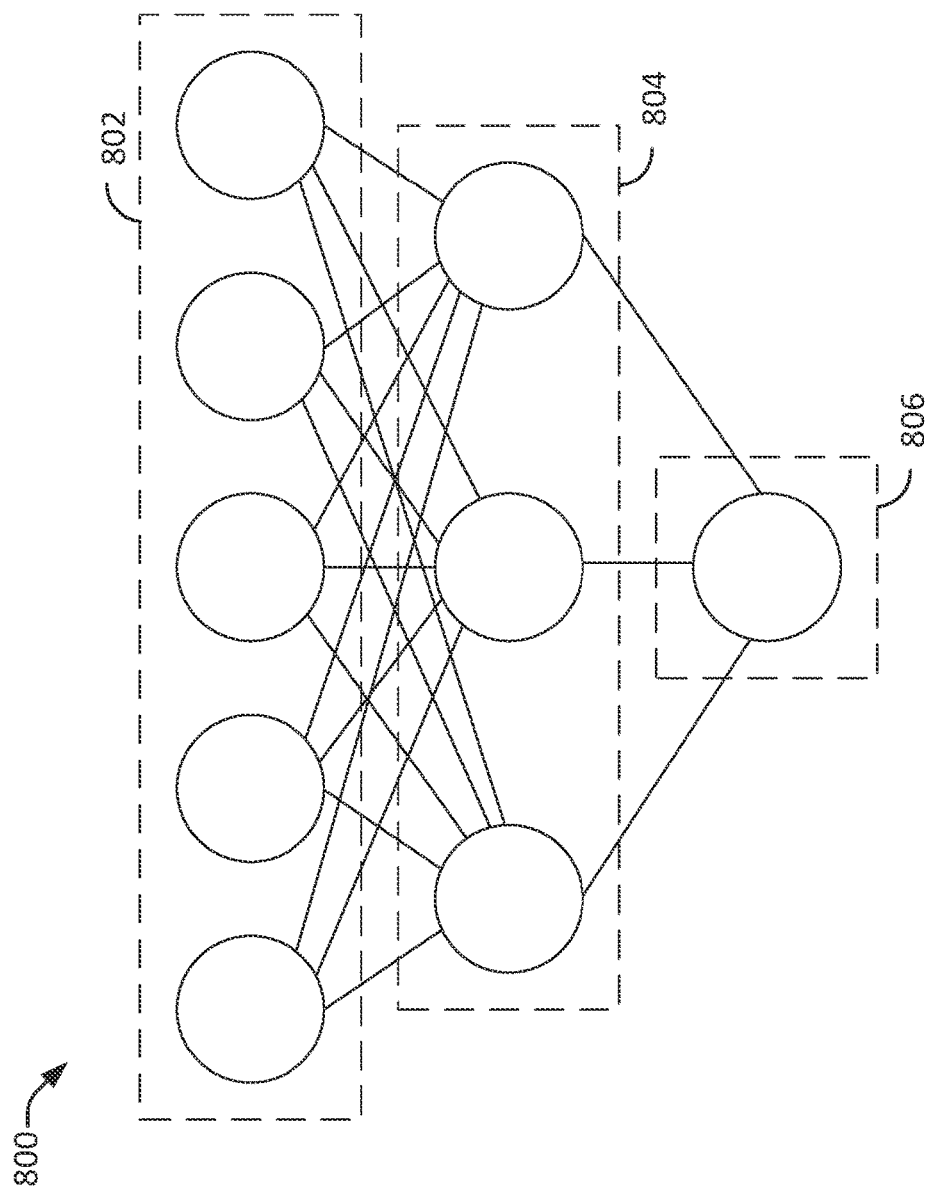
FIG. 8 illustrates an example of a neural network, configured in accordance with some embodiments.

FIG. 8 illustrates an example of a neural network, configured in accordance with some embodiments. FIG. 8 illustrates a neural network 800 that includes input layer 802, hidden layers 804, and output layer 806. Neural network 800 may be a machine learning network that may be trained to perform the techniques described herein (e.g., determining a predicted location of a user and/or providing location groups for the user).

Neural network 800 may be trained with inputs. Input layer 802 may include such inputs. Such inputs may include, for example, regulations, requirements, forms (e.g., example blank or filled out forms), regulation interpretations (e.g., Westlaw® commentary), returns data, completed compliance replies, and/or other such data described herein. Hidden layers 804 may be one or more intermediate layers where logic is performed to determine various aspects of the data (e.g., conversion of a plurality of regulations utilizing different vocabulary to standardized vocabulary). Output layer 806 may result from computation performed within hidden layers 804 and may output, for example, forms, workflows, regulation and requirement interpretations, audit results, and/or other such outputs.

Machine learning may be utilized to determine parameters of the techniques described herein and/or to perform the techniques themselves. In various embodiments, machine learning may continuously or periodically refine the determinations based on data received (e.g., additional jurisdiction data received).

Figure 9:
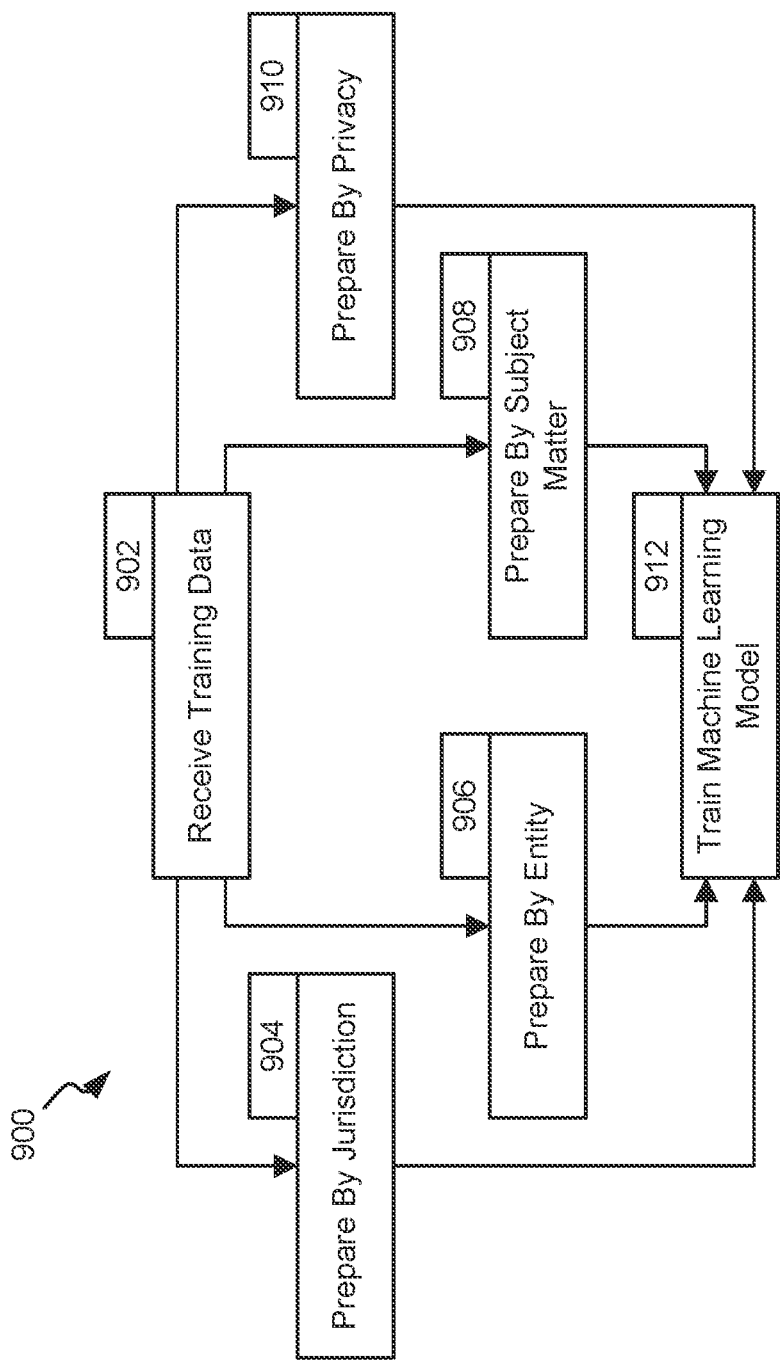
FIG. 9 is a process flowchart illustrating a machine learning compliance dataflow management training technique, in accordance with some embodiments.

FIG. 9 is a process flowchart illustrating a machine learning compliance dataflow management training technique, in accordance with some embodiments. FIG. 9 illustrates technique 900 for training a machine learning model to perform techniques described herein.

In 902, training data may be received. The training data may be data specifically prepared for training the machine learning model and/or may be real data used for training the machine learning model. In certain embodiments that utilize real data, the data may be sanitized (e.g., sensitive information may be removed), before the data is then utilized to train the machine learning model.

The training data may then be prepared in a plurality of different manners. Preparing the training data in a plurality of different manners may include preparing multiple copies of the training data, each of which may then be prepared according to the different manners. In various embodiments, the training data may include a plurality of datapoints. Each datapoint may be, for example, a blank or completed compliance request and may include a plurality of elements. Such a plurality of elements may include elements providing information associated with one or more of a jurisdiction (e.g., indication of the area that care was provided), a compliance entity (e.g., entity requesting compliance), a subject matter (e.g., the type of care provided), privacy level (e.g., sensitivity of data), and/or other such element. Such elements may be utilized for preparation of training data.

In 904, the training data may be prepared based on jurisdiction. In various embodiments, the various portions of the training data may indicate associated jurisdictions. Thus, for example, the training data may include the actual language of regulations and/or requirements as well as commentary and/or standardized language interpretations of the regulations and/or requirements. Each regulation and/or requirement may be associated with one or more jurisdictions. Preparing the training data by jurisdiction may, for example, allow for the machine learning model to determine trends within languages in jurisdictions and/or patterns in requirements within jurisdictions.

In 906, the training data may be prepared based on entity. In various embodiments, the entity may be, for example, the entity requesting the compliance action and/or providing the requested data. Thus, for example, the compliance entity may be a health insurance provider, a healthcare services provider, a billing entity, a private practitioner, an employee, a service receiver, a human resources employee, and/or another such person or entity. Each portion of the training data may be associated with one or more such entities. For example, in various embodiments, the training data may include filled out forms and each form of the training data may be associated with the compliance entity that filled out the form. In another embodiment, certain regulations or requirements may be associated with certain parties or categories of parties (e.g., insurance providers) and the training data may be prepared accordingly. Preparing the training data by the identity of the entity may, for example, allow for the machine learning model to determine trends in how different compliance entities provide information, allowing for responses between compliance entities to be standardized.

In 908, the training data may be prepared according to subject matter. For example, the various portions of the training data may be prepared according to categories (e.g., the category of the forms) such as insurance claim, post-procedure report, human resources summary, and/or other such categories for forms and data that are associated with regulations and/or requirements. Preparing the training data by subject matter may, for example, allow for the machine learning model to determine typical data that is required for each subject matter, how entities generally respond to forms and/or questions for each subject matter to comply with regulations and/or requirements, the number and types of forms that are generally required for each subject matter, and/or other aspects.

In 910, the training data may be prepared according to privacy level. For example, various data may each be accorded a privacy level depending on their sensitivity (e.g., certain data, such as location of procedure, may not be very sensitive, while other data, such as identification number, may be very sensitive). Based on the privacy level, the machine learning model may be trained to only provide certain information and/or only access certain forms (which may require such information from a user), and/or limit other such actions.

Based on the training data prepared in 904, 906, 908, and 910, the machine learning model may be trained in 912. Training of the machine learning model may include, for example, training the machine learning model to interpret updates to the regulation (e.g., to receive data of updated regulations and determine updates to the forms and/or the workflow due to the regulations, as well as the categorization, such as jurisdiction, of the updated regulations), to determine whether a workflow or a form (blank or filled) is in compliance, to perform audits, and/or perform other such actions.

Figure 10:
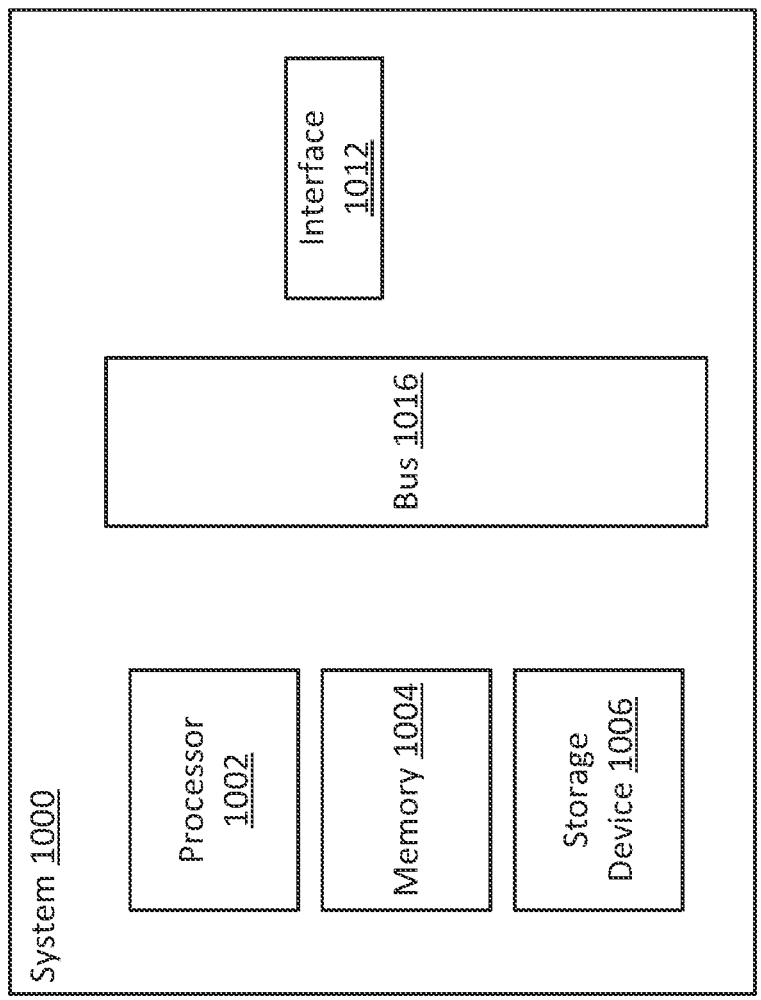
FIG. 10 illustrates a block diagram of an example computing system, in accordance with some embodiments.

FIG. 10 illustrates a block diagram of an example computing system, in accordance with some embodiments. According to various embodiments, a system 1000 suitable for implementing embodiments described herein includes a processor 1002, a memory module 1004, a storage device 1006, an interface 1012, and a bus 1016 (e.g., a PCI bus or other interconnection fabric.) System 1000 may operate as variety of devices such as a server system such as an application server and a database server, a client system such as a laptop, desktop, smartphone, tablet, wearable device, set top box, etc., or any other device or service described herein.

Although a particular configuration is described, a variety of alternative configurations are possible. The processor 1002 may perform operations such as those described herein. Instructions for performing such operations may be embodied in the memory 1004, on one or more non-transitory computer readable media, or on some other storage device. Various specially configured devices can also be used in place of or in addition to the processor 1002. The interface 1012 may be configured to send and receive data packets over a network. Examples of supported interfaces include, but are not limited to: Ethernet, fast Ethernet, Gigabit Ethernet, frame relay, cable, digital subscriber line (DSL), token ring, Asynchronous Transfer Mode (ATM), High-Speed Serial Interface (HSSI), and Fiber Distributed Data Interface (FDDI). These interfaces may include ports appropriate for communication with the appropriate media. They may also include an independent processor and/or volatile RAM. A computer system or computing device may include or communicate with a monitor, printer, or other suitable display for providing any of the results mentioned herein to a user.

Any of the disclosed embodiments may be embodied in various types of hardware, software, firmware, computer readable media, and combinations thereof. For example, some techniques disclosed herein may be implemented, at least in part, by non-transitory computer-readable media that include program instructions, state information, etc., for configuring a computing system to perform various services and operations described herein. Examples of program instructions include both machine code, such as produced by a compiler, and higher-level code that may be executed via an interpreter. Instructions may be embodied in any suitable language such as, for example, Java, Python, C++, C, HTML, any other markup language, JavaScript, ActiveX, VBScript, or Perl. Examples of non-transitory computer-readable media include, but are not limited to: magnetic media such as hard disks and magnetic tape; optical media such as flash memory, compact disk (CD) or digital versatile disk (DVD); magneto-optical media; and other hardware devices such as read-only memory ("ROM") devices and random-access memory ("RAM") devices. A non-transitory computer-readable medium may be any combination of such storage devices.

In the foregoing specification, various techniques and mechanisms may have been described in singular form for clarity. However, it should be noted that some embodiments include multiple iterations of a technique or multiple instantiations of a mechanism unless otherwise noted. For example, a system uses a processor in a variety of contexts but can use multiple processors while remaining within the scope of the present disclosure unless otherwise noted. Similarly, various techniques and mechanisms may have been described as including a connection between two entities. However, a connection does not necessarily mean a direct, unimpeded connection, as a variety of other entities (e.g., bridges, controllers, gateways, etc.) may reside between the two entities.

In the foregoing specification, reference was made in detail to specific embodiments including one or more of the best modes contemplated by the inventors. While various embodiments have been described herein, it should be understood that they have been presented by way of example only, and not limitation. For example, some techniques and mechanisms are described herein in the context of fulfillment. However, the disclosed techniques apply to a wide variety of circumstances. Particular embodiments may be implemented without some or all of the specific details described herein. In other instances, well known process operations have not been described in detail in order not to unnecessarily obscure the techniques disclosed herein. Accordingly, the breadth and scope of the present application should not be limited by any of the embodiments described herein, but should be defined only in accordance with the claims and their equivalents.

The invention claimed is:

1. A system comprising:
a jurisdiction database;
a returns database, configured to store returns data comprising completed workflows, wherein a single completed workflow is configured to allow for completion of a plurality of healthcare compliance forms across a plurality of jurisdictions;
a communication module;
a workflow module, communicatively coupled to the jurisdiction database, the returns database, and the communication module, the workflow module configured to perform workflow operations comprising:
receive a compliance request, the compliance request identifying a plurality of jurisdictions;
communicate, based on the compliance request, a workflow configured to receive data directed to meeting healthcare compliance requirements for each of the plurality of jurisdictions, wherein the workflow is a single interface that combines a plurality of different healthcare compliance forms of the plurality of jurisdictions, and wherein the workflow, as a single interface that combines a plurality of different healthcare compliance forms of the plurality of jurisdictions, is configured to conserve memory and processing resources compared to selecting the plurality of different healthcare compliance forms;

communicate, with the communication module, the workflow to a first entity;

receive, with the communicate module and from the first entity, a completed workflow; and store the completed workflow within the returns database; and an automated auditor, communicatively coupled to the jurisdiction database, the returns database, and the communication module, the automated auditor configured to perform auditing operations comprising:

determining that an audit condition associated with the first entity has been met;

determining, from first returns data associated with the first entity from the returns database, a first jurisdiction associated with the first entity, wherein the first returns data comprises the completed workflow;

obtaining jurisdiction requirement data associated with the first jurisdiction from the jurisdiction database;

analyzing the jurisdiction requirement data to determine compliance requirements for the first jurisdiction;

determining, based on the first returns data and the compliance requirements, a compliance status for the first entity; and providing, with the communication module, the compliance status to a user device associated with the first entity.

2. The system of claim 1, further comprising:
a role/permission module, configured to perform permission operations comprising:

receiving an audit request from the automated auditor, the audit request identifying an audit subject and the first entity;

obtaining second returns data from the returns database, the second returns data associated with the audit subject and the first entity and comprising permission data;

determining, based on the permission data, that the automated auditor is authorized to audit the audit subject of the first entity; and provide data to the returns database to allow the automated auditor to access the returns data.

3. The system of claim 1, wherein the determining that the audit condition associated with the first entity has been met comprises determining, from jurisdiction data of the jurisdiction database, that a milestone condition has been met.

4. The system of claim 1, wherein the determining that the audit condition associated with the first entity has been met comprises receiving updated jurisdiction data associated with the first jurisdiction.

5. The system of claim 1, wherein the determining that the audit condition associated with the first entity has been met comprises receiving an audit request from the user device.

6. The system of claim 1, wherein the compliance status is a determination that the first entity is within compliance.

7. The system of claim 1, wherein the compliance status is a determination that the first entity is non-compliant.

8. The system of claim 7, further comprising a workflow database, wherein the auditing operations further comprise:

determining, based on the determination that the first entity is non-compliant and based on the jurisdiction requirement data, a requirement for compliance;

obtaining workflow data from the workflow database; and determining, based on the workflow data and the requirement for compliance, a compliance action, wherein the compliance status comprises the compliance action.

9. The system of claim 8, wherein the auditing operations further comprise:

receiving, with the communication module from the user device, user data associated with the compliance action.

10. The system of claim 1, wherein the compliance status comprises a compliance score.

11. A system comprising:
an Application Programming Interface (API) gateway, configured to perform first operations comprising:

receiving a first API request from a user device, wherein the first API request comprises authentication data;

determining validity of the authentication data; and providing, based on determining the validity of the authentication data, the first API request to a compliance platform; and the compliance platform, comprising:
one or more API modules, comprising at least a workflow API module;
a memory; and
a processor, configured to receive instructions from the memory to perform second operations comprising:

receiving the first API request from the API gateway;

determining that the first API request comprises a request to access the workflow API module; and providing the user device with access to the workflow API module, wherein the workflow API module is configured to:

receive a first compliance request comprising jurisdiction data identifying a plurality of jurisdictions for compliance;

analyze the jurisdiction data to determine the plurality of jurisdictions for compliance;

obtain, based on the plurality of jurisdictions for compliance, jurisdiction requirement data associated with each of the plurality of jurisdictions;

analyze the jurisdiction requirement data to determine form requirements for compliance, wherein the form requirements is associated with a plurality of different healthcare compliance forms of the plurality of jurisdictions; and create a first workflow based on the form requirements for compliance, wherein the first workflow is configured to receive data directed to meeting healthcare compliance requirements for each of the plurality of jurisdictions, and wherein the first workflow is a single interface that combines the plurality of different healthcare compliance forms of the plurality of jurisdictions, wherein a single completed workflow is configured to allow for completion of the plurality of healthcare compliance forms across the plurality of jurisdictions, and, wherein the first workflow, as a single interface that combines a plurality of different healthcare compliance forms of the plurality of jurisdictions, is configured to conserve memory and processing resources compared to selecting the plurality of different healthcare compliance forms; and provide the first workflow.

12. The system of claim 11, wherein the creating the first workflow comprises:
   obtaining, based on the determined form requirements for compliance, first form data;
   obtaining, based on the determined form requirements for compliance, first workflow data associated with the jurisdictions for compliance; and
   modifying, based on the first workflow data, the first form data to create the first workflow.

13. The system of claim 12, wherein the first form data is obtained from a form database, and wherein the first workflow data is obtained from a workflow database.

14. The system of claim 13, further comprising:
   the form database; and
   the workflow database.

15. The system of claim 11, wherein the workflow API module is configured to be integrated within one or more programs associated with the user device.

16. The system of claim 11, wherein the one or more API modules are further configured to:
   receive regulations and/or requirements from compliance entities associated with the plurality of jurisdictions;
   analyze the regulations and/or requirements to determine the jurisdiction requirement data associated with the plurality of jurisdictions; and
   communicate the jurisdiction requirement data for storage.

17. The system of claim 16, wherein the jurisdiction requirement data is communicated to a jurisdiction database.

18. The system of claim 17, further comprising:
   the jurisdiction database.

19. The system of claim 11, wherein the workflow operations further comprise:
   create the workflow.

20. The system of claim 19, wherein the creating the workflow comprises:
   analyze the compliance request to determine the plurality of jurisdictions;
   obtain, based on the plurality of jurisdictions, jurisdiction requirement data associated with each of the plurality of jurisdictions;
   determine form requirements for compliance within each of the plurality of jurisdictions, wherein the form requirements is associated with a plurality of different healthcare compliance forms of the plurality of jurisdictions; and
   create the workflow based on the form requirements for compliance.

* * * * *